(12) United States Patent  
Keppler et al.

(10) Patent No.: US 8,975,289 B2  
(45) Date of Patent: Mar. 10, 2015

(54) BENZYL ARALKYL ETHER COMPOUNDS, METHOD FOR PREPARING SAME, INTERMEDIATE COMPOUNDS, USE OF SAID COMPOUNDS, METHOD FOR TREATMENT AND/OR PREVENTION, PHARMACEUTICAL COMPOSITION AND MEDICAMENT CONTAINING SAME

(75) Inventors: Artur Franz Keppler, Santo André - SP (BR); Sérgio Luiz Sacurai, São Paulo - SP (BR); Marcio Henrique Zaim, São Paulo - SP (BR); Carlos Eduardo da Costa Touzarim, São Paulo - SP (BR)

(73) Assignee: Biolab Sanus Farmaceutical Ltda., Sao Paulo (BR)

( * ) Notice: Subject to any disclaimer, the term of this patent is extended or adjusted under 35 U.S.C. 154(b) by 0 days.

(21) Appl. No.: 13/389,741

(22) PCT Filed: Aug. 27, 2010

(86) PCT No.: PCT/BR2010/000276  
§ 371 (c)(1),  
(2), (4) Date: Apr. 20, 2012

(87) PCT Pub. No.: WO2011/022798  
PCT Pub. Date: Mar. 3, 2011

(65) Prior Publication Data  
US 2012/0196908 A1 Aug. 2, 2012

(30) Foreign Application Priority Data  
Aug. 28, 2009 (BR) .................................. 0904249

(51) Int. Cl.  
*A61K 31/4174* (2006.01)  
*C07D 233/54* (2006.01)  
*C07D 249/08* (2006.01)  
*C07C 22/08* (2006.01)  
*C07D 233/22* (2006.01)  
*C07D 403/12* (2006.01)  
*A61K 9/00* (2006.01)  
*A61K 47/14* (2006.01)

(52) U.S. Cl.  
CPC ............ *C07D 249/08* (2013.01); *C07D 233/54* (2013.01); *A61K 31/4174* (2013.01); *C07C 22/08* (2013.01); *C07D 233/22* (2013.01); *C07D 403/12* (2013.01); *A61K 9/0014* (2013.01); *A61K 47/14* (2013.01)  
USPC ...................... 514/396; 548/341.1

(58) Field of Classification Search  
None  
See application file for complete search history.

(56) References Cited

U.S. PATENT DOCUMENTS

| 3,717,655 A | 2/1973 | Godefroi et al. |
| 4,277,475 A * | 7/1981 | Vickery .................. 514/254.07 |
| 5,461,068 A | 10/1995 | Thaler et al. |

FOREIGN PATENT DOCUMENTS

| DE | 1940388 A1 | 2/1970 |
| EP | 0 065 385 A2 | 11/1982 |
| EP | EP 0 123 218 A2 | 10/1984 |
| FR | 2334676 A1 | 7/1977 |

(Continued)

OTHER PUBLICATIONS

Guven et al., "Synthesis and antimicrobial activity of some novel phenyl and benzimidazole substituted benzyl ether". Bioorganic and Medicinal Chemistry letters 2007, 17, 2233-2236.*

(Continued)

*Primary Examiner* — Michael Barker  
*Assistant Examiner* — Po-Chih Chen  
(74) *Attorney, Agent, or Firm* — Arent Fox LLP

(57) ABSTRACT

This invention describes new antifungal compounds that are aralkyl benzyl ethers of the formula (I):

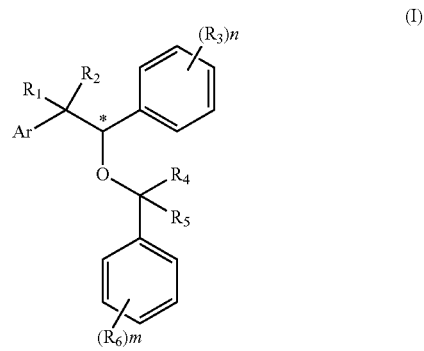

Figure 1:
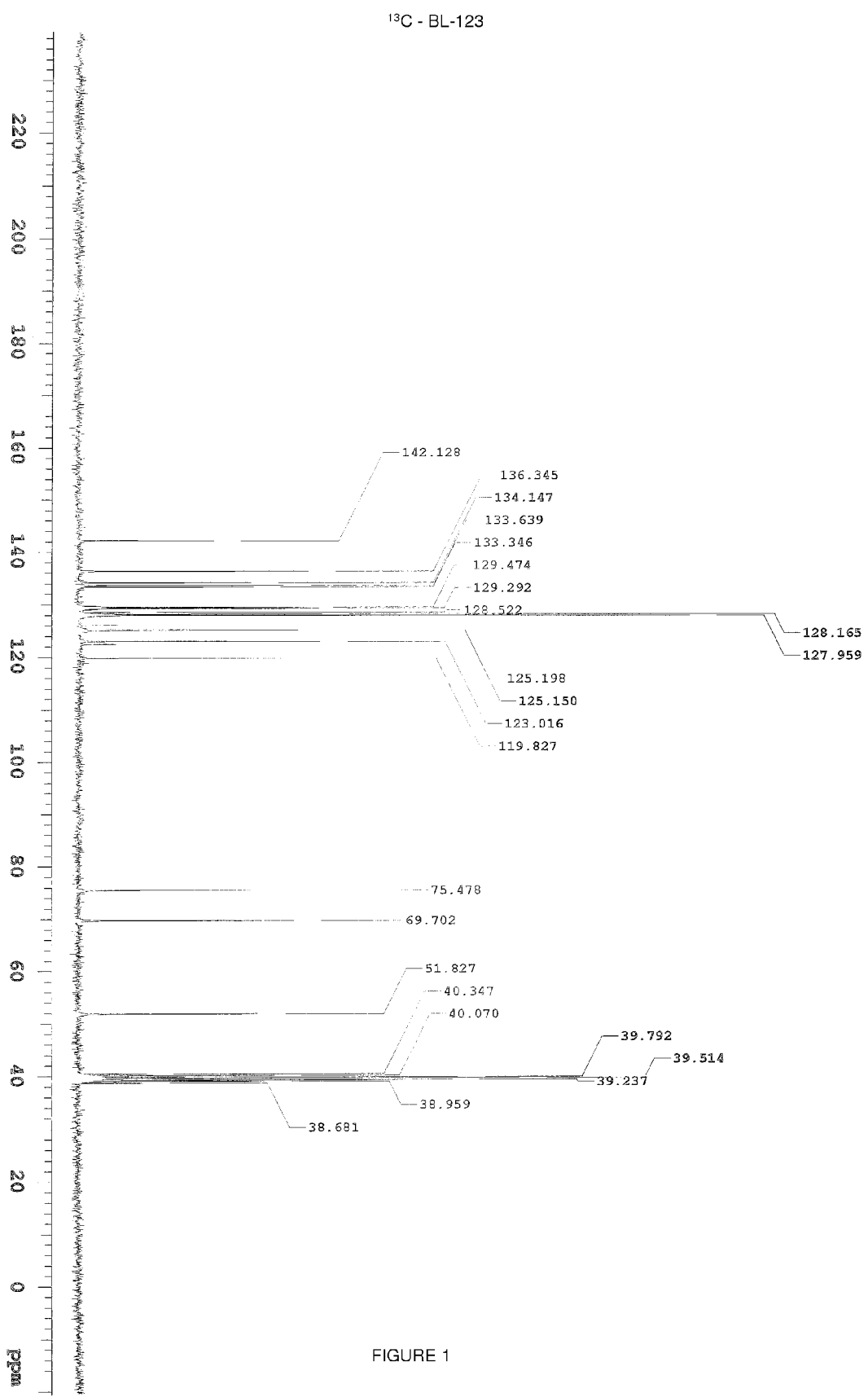

where Ar represents aryl, imidazolil, 1,2,4-triazolyl, benzimidazolil;  
$R_1$, $R_2$, $R_4$ and $R_5$ are independently hydrogen, halogen, $C_{1-6}$ alkyl;  
$R_3$ represents halogen, $C_{1-6}$ alkyl or O—R' where R' represents hydrogen or lower alkyl;  
$R_6$ represents aryl, substituted aryl, trifluoromethyl, trichloromethyl or O—R' where R' represents hydrogen or lower alkyl; being the substituents of the aryl a halogen or a radical tetrazolyl;  
n and m represent independently an integer between 0 and 5;  
With the proviso that when Ar is imidazolil, $R_3$ is chlorine, $R_6$ is p-phenyl and $R_1$, $R_2$, $R_4$ and $R_5$ are hydrogen, n must be different from 2.  
When n and m are not 0 and 1, $R_3$ or $R_6$ can be represented by substituents not necessarily equal.

3 Claims, 4 Drawing Sheets

(56) References Cited

FOREIGN PATENT DOCUMENTS

| WO | WO 96/39835 A1 | | 12/1996 |
|---|---|---|---|
| WO | WO2006081327 | * | 8/2006 |
| WO | WO2006082588 | * | 8/2006 |
| WO | WO 2009/013480 A2 | | 1/2009 |
| WO | WO 2009/081117 A1 | | 7/2009 |
| WO | WO 2010/007381 A1 | | 1/2010 |
| WO | WO 2010/025459 A2 | | 3/2010 |

OTHER PUBLICATIONS

Grant & Hackh's Chemical Dictionary (5th Ed. 1987) at p. 148.*

Cirilli et al., Comparative study between the polysaccharide-based Chiralcel OJ and Chiralcel OD CSPs in chromatographic enantioseparation of imidazole analogues of Fluoxetine and Miconazole. Journal of Separation Science, 2005, 28, 627-634.*

Silvestri et al., Imidazole Analogues of Fluoxetine, A Novel Class of Anti-Candida Agents. Journal of Medicinal Chemistry, 2004, 47, 3924-3926.*

Supplementary European Search Report for EP 10 81 1042 dated Dec. 18, 2012, pp. 1-9.

Wahbi Y et al: "Aromatic ethers of 1-aryl 2-(1H-azolyl)ethanol; study of antifungal activity", European Journal of Medicinal Chemistry, Editions Scientifique Elsevier, Paris, FR, vol. 30, No. 12, Jan. 1, 1995, pp. 955-962, XP004040225, ISSN: 0223-5234, DOI:10.1016/0223-5234(96)88315-2 whole document, specially examples 4a and 5b in Table III.

Fioravanti et al.: "A New Series of Miconazole Analogs Synthesis and In Vitro Antifungal and Antimycobacterial Activities", Medicinal Chemistry Research, vol. 9, No. 3, 1999, pp. 162-175, XP009165671, whole document, specially compounds 2e, 2f, 2g, 2h.

Nardi et al.: "New alpha-Aryl-beta,N-imidazolylethyl Benzyl and Naphthylmethyl Ethers with Antimycotic and Antibacterial Activity", Arzneimittel Forschung, vol. 31, No. 12, 1981, pp. 2123-2126, XP001526324, Whole Document Specially Compounds 1-4.

Manetti et al., Building a pharacophore model for a novel class of antitubercular compounds, Il Farmaco, Jun. 12, 2000, pp. 484-491, vol. 55.

* cited by examiner

BENZYL ARALKYL ETHER COMPOUNDS, METHOD FOR PREPARING SAME, INTERMEDIATE COMPOUNDS, USE OF SAID COMPOUNDS, METHOD FOR TREATMENT AND/OR PREVENTION, PHARMACEUTICAL COMPOSITION AND MEDICAMENT CONTAINING SAME

CROSS-REFERENCE TO RELATED APPLICATIONS

This application is a National Stage entry of International Application No. PCT/BR2010/000276, filed Aug. 27, 2010, which claims priority to Brazilian Patent Application No. P10904249-0, filed Aug. 28, 2009, the disclosure of the prior application are incorporated in their entirety by reference.

FIELD OF THE INVENTION

The present invention relates to compounds that are aralkyl benzyl ethers described in formula (I), their enantiomers, their diastereoisomers, their pro-drugs, esters, their pharmaceutically acceptable salts, their pharmaceutically acceptable solvates, and/or mixtures thereof in any proportions of these compounds and/or derivatives, to processes for the preparation of these compounds, intermediate compounds, pharmaceutical compositions comprising such compounds and/or derivatives, medicines including said compounds and/or derivatives, as well as to the uses of these compounds and/or derivatives in the treatment and/or prevention of conditions and/or diseases caused by microorganisms, such as fungi, bacteria and/or protozoa, for the inhibition of proliferation and/or survival of said microorganisms, for the treatment and/or prevention of colonization of microorganisms in an individual, and for the manufacture of a medicine.

The present invention also relates to the method of treatment and/or prevention of conditions in a mammal caused by fungi and/or other microorganisms such as bacteria and protozoa using aralkyl benzyl ethers compounds described in the formula (I) and, more particularly, compounds 1-[2-(2,4-dichlorophenyl)-2-{[4-(trifluoromethyl)benzyl]oxy}ethyl] 1H-imidazole and 1-[2-(2,4-dichlorophenyl)]-2-({4-[(2-phenyl)-2H-tetrazole]benzyl}oxy)ethyl]-1H-imidazole.

The present invention encompasses aralkyl benzyl ether compounds described in formula (I) and mixtures thereof in any proportions, their pharmaceutically acceptable salts, and pharmaceutical compositions containing them. More particularly, the present invention relates to the use of aralkyl benzyl ether compounds described in formula (I) and, more particularly, the compounds 1-[2-(2,4-dichlorophenyl)-2-{[4-(trifluoromethyl)benzyl]oxy}ethyl]-1H-imidazole and 1-[2-(2, 4-dichlorophenyl)]-2-({4-[(2-phenyl)-2H-tetrazole]benzyl}oxy)ethyl]-1H-imidazole as fungistatic and/or fungicide antifungals.

FUNDAMENTS OF THE INVENTION

The azole compounds are the main agents used in clinical medicine for the treatment and/or prevention of conditions and/or diseases associated with fungi.

The antifungal action of the azole agents commonly occurs through inhibition of ergosterol (ergosta-5,7,22-trien-3β-ol) by the inhibition of proteins involved in the biosynthesis of the same, such as: (a) the enzyme lanosterol 14-alpha-demethylase that belongs to the cytochrome p450 family and is encoded by the ERG11 gene, and (b) delta$^{22}$ desnaturase (encoded by the ERGS gene). Ergosterol is a sterol precursor of vitamin D and a structural component of fungal cell membrane, which can also be found in other microorganisms such as protozoa and bacteria.

Document U.S. Pat. No. 3,705,172 (Bayer), published on Dec. 5, 1972, refers to N-Trityl-imidazol compounds among which the clotrimazole compound represented structurally below, used in medicine practice for the topical treatment of dermatophytes, yeasts and dimorphic and filamentous fungi.

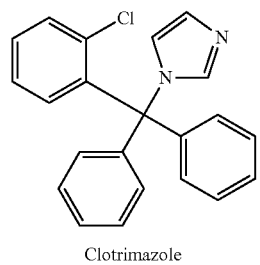 [SMILES: Clc1ccccc1C(c1ccccc1)(c1ccccc1)n1ccnc1]

Clotrimazole

Document U.S. Pat. No. 3,717,655 (Janssen), published on Feb. 20, 1973, refers to derivatives of amines or ariletil-imidazole ethers, which introduced into the medical practice anti-fungal drugs used until today, such as miconazole, econazole, and isoconazol, which are represented as follows:

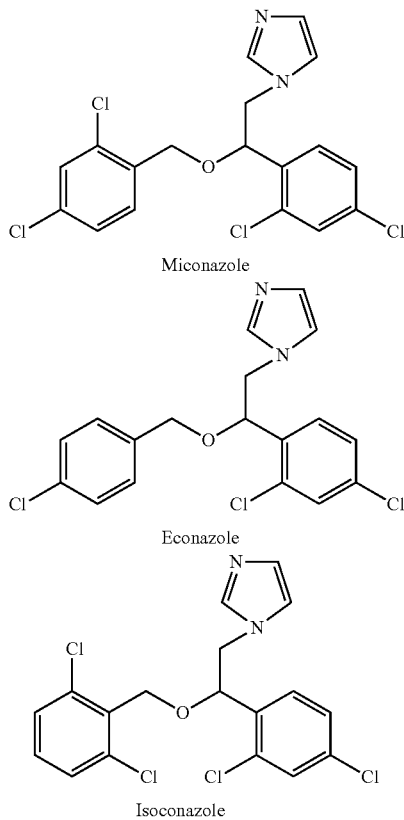

Miconazole

Econazole

Isoconazole

The patent documents U.S. Pat. No. 4,144,346 (Mar. 13, 1979) and U.S. Pat. No. 4,267,179 (May 12, 1981), both from Janssen, describe antifungal compounds derived from (dioxolan)imidazoles among which are the drugs ketoconazole and itraconazole, respectively, used in the current therapy, whose chemical structures are shown below:

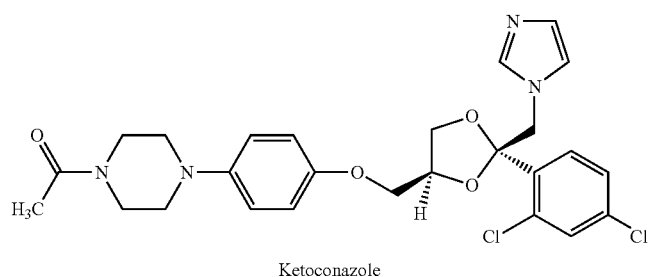

Ketoconazole

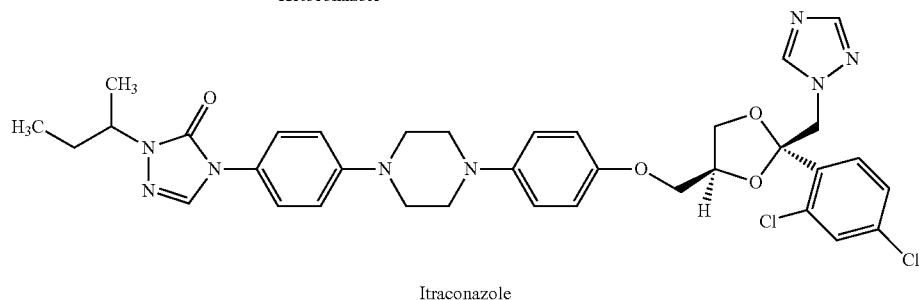

Itraconazole

Document U.S. Pat. No. 4,062,966 (Pfizer) published on Dec. 13, 1977 with regard to new derivative ethers from (aryl ethyil)imidazole, describes the antifungal drug Tioconazole.

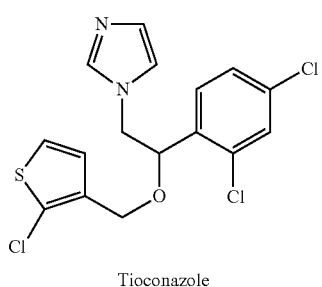 [SMILES: Clc1ccc(C(Cn2ccnc2)OCc2ccsc2Cl)c(Cl)c1]

Tioconazole

Bis-triazole and triazole antifungal compounds are described in the patent document U.S. Pat. No. 4,400,219 (Pfizer), published on Sep. 13, 1983 and in the patent document U.S. Pat. No. 5,278,175 (Pfizer), published on Jan. 11, 1994, clinically used antifungal agents, fluconazole and voriconazole, are disclosed, respectively:

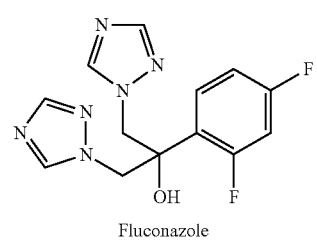

Fluconazole

-continued

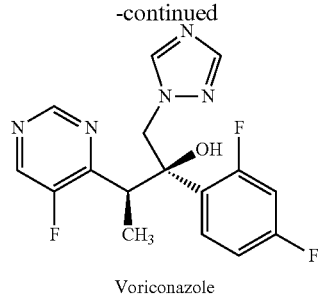

Voriconazole

Interestingly, the prolonged and repeated exposure of fungal strains to antifungal agents may result in resistance of these strains to the action of these agents reducing the efficiency thereof. It is defined as a strain a particular gene variant of a microorganism.

Such resistance may be resulted from different mechanisms such as, but not limited to: (a) modification at the molecular level of the ERG11 gene, (b) overexpression of specific drugs efflux pumps such as CDR (confluence dependent resistance) and MDR (multiple drug resistance), (c) modification of sterol biosynthesis, and (d) reduction in the intracellular concentration of target enzymes.

The resistance problem becomes more relevant in the current epidemiological situation of diseases caused by fungi. It has been observed that in recent decades a significant increase in worldwide incidence of fungal infections in humans has been occurring. Most of this increase is attributed to the prolonged survival of immunocompromised patients and the frequent and/or chronic use of antimicrobial agents.

Thus, most patients who are susceptible to these infections are those with impaired immune function, either directly due to immunosuppression caused by the use of cytotoxic drugs or HIV infection or secondarily, or due to other debilitating diseases such as cancer, acute leukemia, invasive surgical techniques or prolonged exposure to antimicrobial agents.

Particularly, the wide spread of HIV infection contributes to the increase of opportunistic infections caused by fungi which are harmless to healthy individuals, but become pathogenic due to the weakened immune defense of HIV-infected patients.

Therefore, considering the current epidemiological situation of infections caused by these microorganisms and the emergence of pathogenic strains resistant to currently used antifungal drugs, the interest in the development of new compounds becomes evident. It is desirable the development of a compound with a broad-spectrum antifungal activity considering strains and/or species of fungi non-resistant and/or resistant to known drugs.

DESCRIPTION OF THE INVENTION

The present inventions aims on providing new compounds which are useful for treating diseases and/or conditions associated with microorganisms such as fungi, bacteria and/or protozoa, which are aralkyl benzyl ethers, whose chemical structure is shown in formula (I):

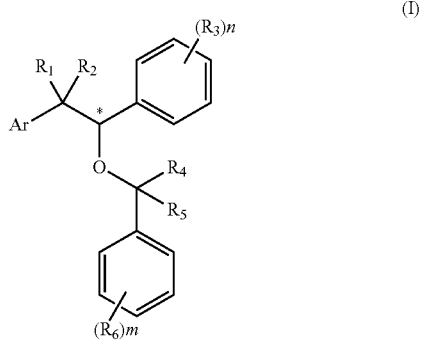

wherein:
Ar represents aryl, imidazolil, 1,2,4-triazolyl and benzimidazolil;
$R_1$, $R_2$, $R_4$ and $R_5$ independently represent hydrogen, halogen, $C_{1-6}$ alkyl;
$R_3$ represents a substituent which is halogen, $C_{1-6}$ alkyl or O—R' wherein R' represents hydrogen or lower alkyl;
$R_6$ represents aryl or substituted aryl, trifluoromethyl, trichloromethyl or O—R' where R' represents hydrogen or lower alkyl; the substituent of the aryl are a halogen or a tetrazolyl radical.
n and m represent independently an integer between 0 and 5;
With the proviso that when Ar is imidazolil, $R_3$ is chlorine, $R_6$ is p-phenyl and $R_1$, $R_2$, $R_4$ and $R_5$ are hydrogen, n must be different from 2; and
When n and m is not 0 and 1, $R_3$ or $R_6$ can be represented by substituents that are not necessarily equal;

The present invention also includes salts, solvates, pro-drugs and pharmaceutically acceptable esters of the compounds described by formula (I) as well as their enantiomers and/or pharmaceutically acceptable diastereomers salts and mixtures thereof in any proportions.

Another objective of this invention is to provide a process for the preparation of aralkyl benzyl ethers compounds described in formula (I), as well as their intermediate compounds used in the synthesis process.

It is also an object of this invention to describe the use of aralkyl benzyl ethers of the present invention or their salts, solvates, pro-drugs, esters, enantiomers and/or pharmaceutically acceptable diastereoisomers or mixtures thereof, to treat and/or prevent, and/or for the manufacture of a medicament for the treatment and/or prevention of conditions and/or diseases caused by microorganisms such as fungi, bacteria and/or protozoa in a eukaryotic organism. Additionally, the compounds of this invention are used to inhibit and/or delay, and/or for the manufacture of a medicine for the inhibition and/or retardation of proliferation and/or survival of microorganisms such as fungi, bacteria and/or protozoa, more particularly of pathogenic microorganisms. In particular, the aim of this invention is the use of aralkyl benzyl ethers described in formula (I) as fungistatic and/or fungicide antifungals.

An additional objective of this invention is to provide a method for the treatment and/or prevention of conditions and/or diseases associated with microorganisms such as fungi, bacteria and/or protozoa, in a mammal in need of such treatment comprising the administration of an effective amount of at least one of the aralkyl benzyl ether compounds described in formula (I) of this invention or their salts, solvates, pro-drugs, esters, enantiomers and/or pharmaceutically acceptable diastereoisomers, or mixtures thereof.

Another objective of this invention is to provide pharmaceutical compositions and medicines comprising an effective amount of at least one of the compounds described by formula (I) or its salts, solvates, pro-drugs, esters, enantiomers and/or pharmaceutically acceptable diastereoisomers, or mixture thereof, as active ingredient and one or more pharmaceutically acceptable excipients.

DESCRIPTION OF FIGURES AND TABLES

FIG. 1: Characterization of the compound obtained by the procedures described in examples 1 and 2 (1-[2-(2,4-dichlorophenyl)-2-{[4-(trifluoromethyl)benzyl]oxy}ethyl]-1H-imidazole (BL-123)) by NMR spectroscopy of carbon 13.

Figure 2:
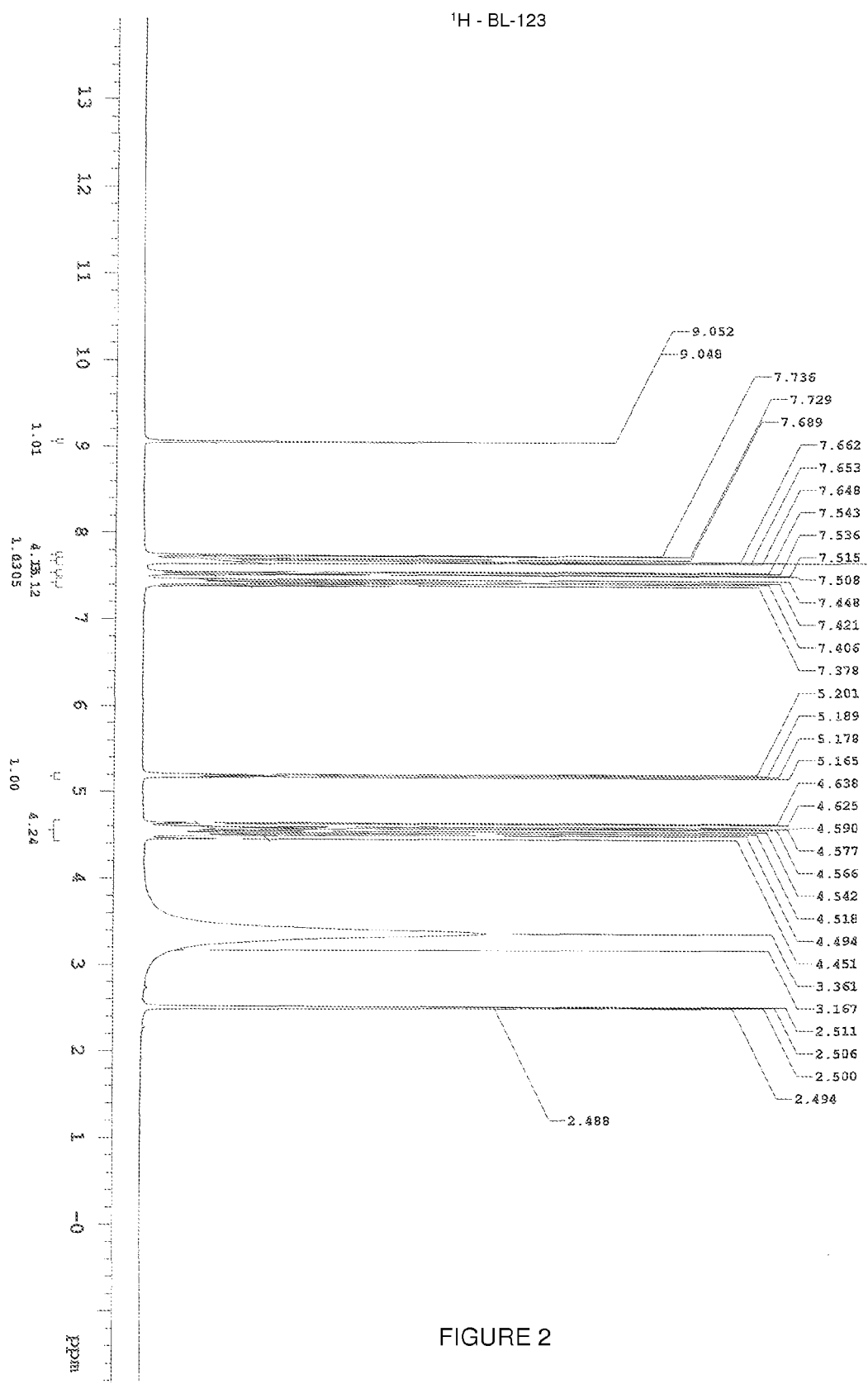

FIG. 2: Characterization of the compound obtained by the procedures described in examples 1 and 2 (1-[2-(2,4-dichlorophenyl)-2-{[4-(trifluoromethyl)benzyl]oxy}ethyl]-1H-imidazole (BL-123)) by NMR spectroscopy of $^1$H.

Figure 3:
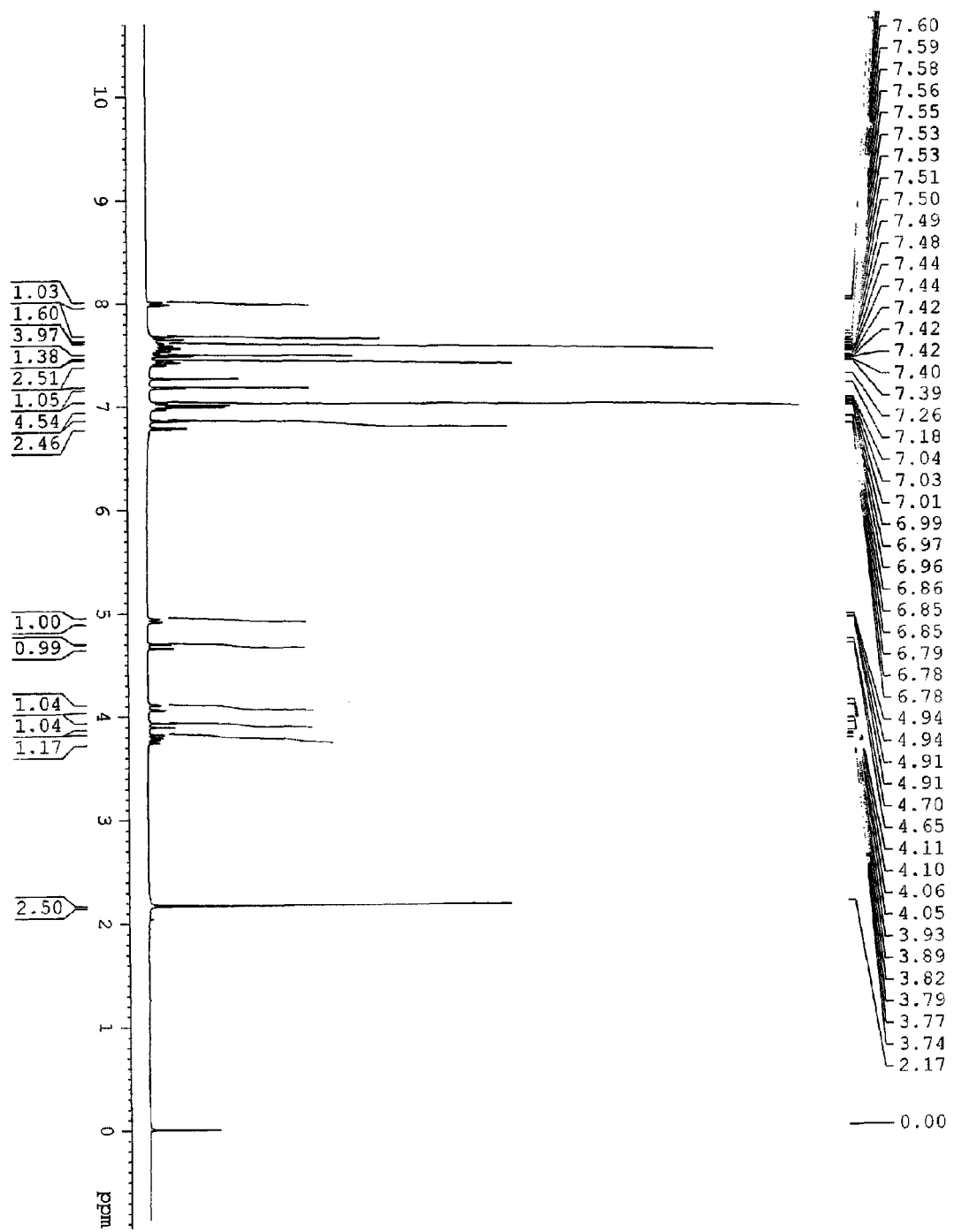

FIG. 3: Characterization of the compound obtained by the procedure described in example 3 (1-[2-(2,4-dichlorophenyl)]-2-({4-[(2-phenyl)-2H-tetrazole]benzyl}oxy)ethyl]-1H-imidazole (BL-137)) by NMR spectroscopy of $^1$H.

Figure 4:
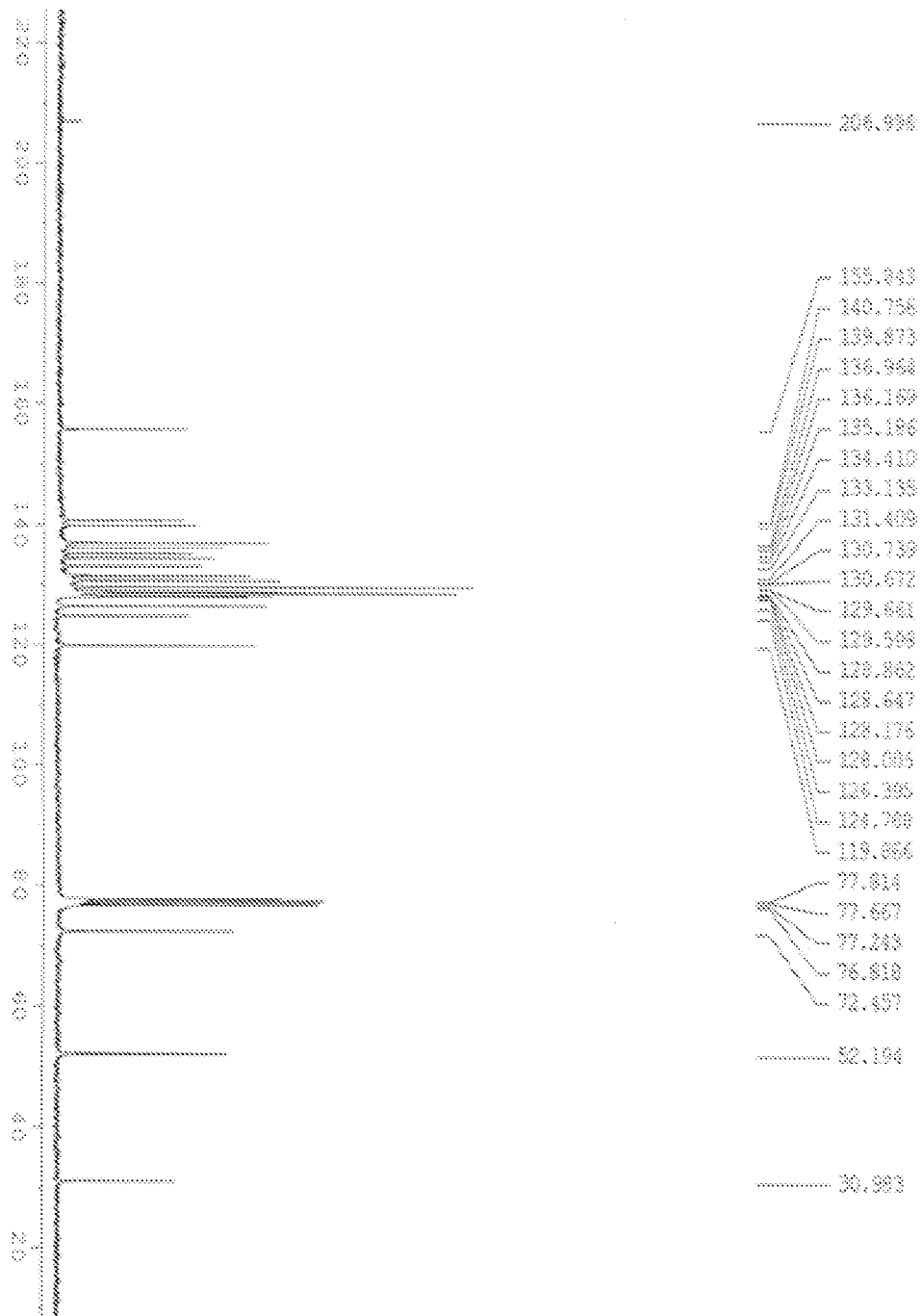

FIG. 4: Characterization of the compound obtained by the procedure described in example 3 (1-[2-(2,4-dichlorophenyl)]-2-({4-[(2-phenyl)-2H-tetrazole]benzyl}oxy)ethyl]-1H-imidazole (BL-137)) by NMR spectroscopy of carbon 13.

Formula (I): Structural formula describing the basic compounds included in this invention, wherein Ar represents aryl, imidazolil, benzimidazolyl; $R_1$, $R_2$, $R_4$ and $R_5$ represent independently hydrogen, halogen, $C_{1-6}$ alkyl, $R_3$ represents halogen, $C_{1-6}$ alkyl or O—R' where R' represents hydrogen or lower alkyl; n and m represent independently an integer between 0 and 5, $R_6$ represents aryl or substituted aryl trifluoromethyl, trichloromethyl, or O—R' where R' represents hydrogen or lower alkyl; being the substituents of the aryl a halogen or a radical tetrazolyl proviso that when Ar is imidazolyl, $R_3$ is chlorine, $R_6$ is p-phenyl and $R_1$, $R_2$, $R_4$ and $R_5$ are hydrogen, n must be different from 2 and when n and m are not 0 and 1, $R_3$ or $R_6$ can be represented by substituents not necessarily equal.

Formulas (Ia), (Ib) and (Ic): basic structural formulas describing the particularly preferred compounds of this invention where $R_3$ is halogen and $R_6$ is a phenyl radical, halogen-phenyl, (tetrazolyl)phenyl, trifluoromethyl, trichloromethyl anywhere in the benzyl ring;

Procedure 1: General scheme of the process of synthesis of compounds of this invention wherein Ar, $R_1$-$R_6$, n and m of formulas (II) and (III) are as described above, and wherein X refers to elements selected from the group consisting of Cl, Br, I, methanesulfonate and toluenesulfonates.

Procedure 2: particular scheme of the synthesis process of this invention for the preparation of the compound BL-123.

Procedure 3: particular scheme of the synthesis process of this invention for the preparation of the compound BL-137.

Table 1: Examples of intermediaries described by formulas II and III that are employed in the preparation of compounds of this invention according to the substituent exemplified in positions Ar, $R_1$, $R_2$, $R_4$, $R_5$, $(R_3)_n$, $R_6$ and m and where the term "prot" represents the protection groups in this invention and "X" represents elements selected from the group consisting of Cl, Br, I, MS (methanesulfonates) and TS (toluenesulfonates).

Table 2: Identification of filamentous fungi strains employed in susceptibility tests to antifungal agents of this invention.

Table 3: Average of the minimum inhibitory concentration (MIC) obtained in four susceptibility experiments of filamentous fungi strains, which are described in Table 2, performed on different days with readings of the results carried out on the fourth and seventh days.

Table 4: Average values of MIC50 (minimum inhibitory concentration necessary to inhibit 50% of strains), MIC 90 (minimum inhibitory concentration to inhibit 90% of strains) and VMICs (variation of minimum inhibitory concentration) for the agents used for susceptibility testing of filamentous fungi to the antifungal agents of this invention.

Table 5: Identification of bacteria and yeast strains employed in susceptibility testing to the antifungal agents of this invention.

Table 6: Minimum Inhibitory Concentration of the antifungal agents tested against strains of yeasts and bacteria described in Table 5.

Table 7: Example of formulation as a cream containing the compound BL-123 described in this invention.

Table 8: Example of the powder formulation comprising the compound BL-123 described in this invention.

Table 9: Example of formulation in the form of lotion comprising the compound BL-123 described in this invention.

DETAILED DESCRIPTION OF THE INVENTION

This invention discloses new compounds which are useful for treating conditions caused by fungi and/or other microorganisms such as bacteria and protozoa, which are aralkyl benzyl ethers, described by the formula (I) and its salts, solvates, pro-drugs and pharmaceutically acceptable esters:

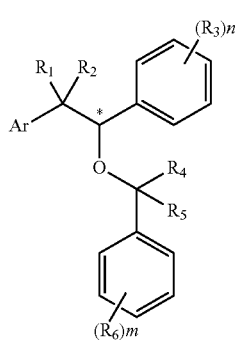

wherein:
Ar represents aryl, imidazolyl, 1,2,4-triazolyl, benzimidazolyl;

$R_1$, $R_2$, $R_4$, and $R_5$ represent independently hydrogen, halogen, $C_{1-6}$ alkyl;

$R_3$ represents a substituent which is halogen, $C_{1-6}$ alkyl or O—R' where R' represents hydrogen or lower alkyl;

$R_6$ represents aryl or substituted aryl, trifluoromethyl, trichloromethyl or O—R' where R' represents hydrogen or lower alkyl, the substituent of the aryl and a halogen or a tetrazolyl radical;

n and m independently represent an integer between 0 and 5; With the proviso that when Ar is imidazolyl, $R_3$ is chlorine, $R_6$ is p-phenyl and $R_1$, $R_2$, $R_4$ and $R_5$ represent hydrogen, n must be different from 2; and When n and m are different than 0 and 1, $R_3$ or $R_6$ can be represented by substituents that are not necessarily equal; and When the substituents $R_1$, $R_2$, $R_4$ and $R_5$ are simultaneously equal to hydrogen and $R_6$ is trifluoromethyl or trichloromethyl, the 1,2,4-triazolyl radical must be connected to the main structure by distinct position of 2, as follows

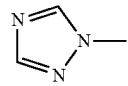

Bond in position 2

The compounds of formula (I) have one or more asymmetric centers and thus, enantiomer and/or diastereoisomer salts may exist. In particular, a chiral center is shown with an asterisk in the description of formula (I). Therefore, this invention also covers the enantiomers of the compounds of formula (I) in their individual separate ways and/or in the form of racemic mixtures or non-racemic mixtures with enantiomeric excess in any proportion.

The pharmaceutically acceptable salts of formula (I) compounds are formed by adding pharmaceutically acceptable acids. Examples of salts include, but are not limited to, nitrate, chloride, bromhydrate, sulfate, bisulfate, phosphate, hydrogen phosphate, acetate, benzoate, succinate, fumarate, maleate, lactate, citrate, tartrate, gluconate, metasulfonate, benzenesulfonate and p-toluenesulfonate salts.

Considering the description of the compounds of formula (I), the term "aryl" described in Ar represents a phenyl group or a phenyl group substituted with 1 to 5 halogens, 1 to 5 ($C_{1-6}$ alkyl) and/or 1 to 5 ($C_{1-6}$ alkoxy).

The term "alkyl" represents the main alkyl chain or, when available, a branched alkyl chain of the groups it represents. Examples of "alkyl" groups of this invention include, but are not limited to: methyl, ethyl, n-propyl, i-propyl, n-butyl, s-butyl, t-butyl, n-pentyl, s-pentyl, t-pentyl, i-pentyl, n-hexyl, s-hexyl or t-hexyl. The term "lower alkyl" refers to alkyl groups as defined above, containing 1 to 6 carbons.

The term "halogen" represents fluorine, chlorine, bromine or iodine atoms.

When $R_3$ or $R_6$ represent a group "O—R" or "aryl" or "trifluoromethyl" or "trichloromethyl", such substituents may be bond to any available position of the phenyl group at one or more positions.

A particular group of compounds of the present invention is selected from the compounds described by formula (I) wherein $R_1$, $R_2$, $R_4$ and $R_5$ are hydrogen, $R_3$ is halogen, n is an integer from 0 to 2, so that, when n is equal to 0, the aromatic ring that is bond to $R_3$ is not substituted, m is 1, $R_6$ is a phenyl, halogen-phenyl, (tetrazolyl)phenyl, trifluoromethyl or trichloromethyl radical in any position of the benzyl ring, and Ar is an imidazolyl group or 1,2,4-triazolyl, wherein when n and m are different from 0 and 1, $R_3$ or $R_6$ can be represented by substituents that are not necessarily equal and/or when $R_6$ is a trifluoromethyl or trichloromethyl, the 1,2,4-triazolyl radical must be bond to the main structure by a position distinct from 2. This particular group of compounds of the present invention is represented by formula (Ia), (Ib) and (Ic), as follows, wherein the substitutions $R_3$ and $R_6$ are as defined in this paragraph:

More specifically, the preferred compounds of this invention are compounds selected from the group consisting of:

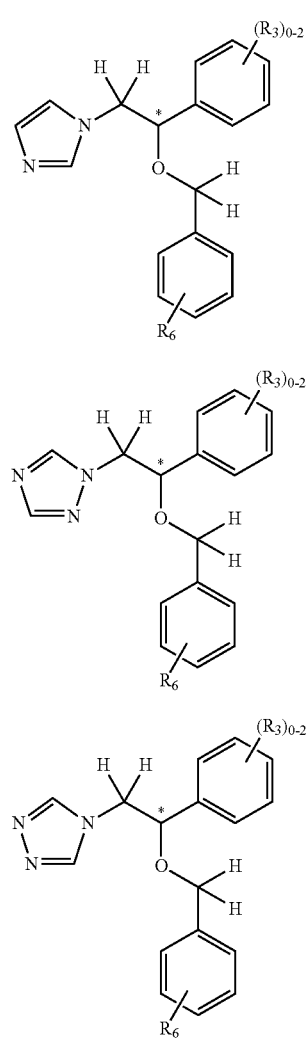

1-[2-(2,4-dichlorophenyl)-2-{[3-(trifluoromethyl)benzyl]oxy}ethyl]-1H-imidazole
1-[2-(2,4-dichlorophenyl)-2-{[3-(trichloromethyl)benzyl]oxy}ethyl]-1H-imidazole
1-[2-(2,4-dichlorophenyl)-2-{[4-(trifluoromethyl)benzyl]oxy}ethyl]-1H-imidazole
1-[2-(2,4-dichlorophenyl)-2-{[4-(trichloromethyl)benzyl]oxy}ethyl]-1H-imidazole
1-[2-(2,4-dichlorophenyl)-2-{[3-(trifluoromethyl)benzyl]oxy}ethyl]-4H-1,2,4-triazole
1-[2-(2,4-dichlorophenyl)-2-{[3-(trichloromethyl)benzyl]oxy}ethyl]-4H-1,2,4-triazole
1-[2-(2,4-dichlorophenyl)-2-{[4-(trifluoromethyl)benzyl]oxy}ethyl]-4H-1,2,4-triazole
1-[2-(2,4-dichlorophenyl)-2-{[4-(trichloromethyl)benzyl]oxy}ethyl]-4H-1,2,4-triazole
1-[2-(2,4-dichlorophenyl)]-2-({4-[(2-phenyl)-2H-tetrazole]benzyl}oxy)ethyl]-1H-imidazole
1-[2-[(4'-clorobifenil-4-yl)methoxy]-2-(2,4-dichlorophenyl)ethyl]-1H-imidazole
1-[2-(biphenyl-4-ilmetoxi)-2-(2,4-dichlorophenyl)ethyl]-1H-imidazole
1-[2-(2,4-dichlorophenyl)]-2-({4-[(2-phenyl)-2H-tetrazole]benzyl}oxy)ethyl]-1H-1,2,4-triazole
1-{2-[(4'-clorobifenil-4-yl)methoxy]-2-(2,4-dichlorophenyl)ethyl}-1H-1,2,4-triazole
1-[2-(biphenyl-4-ilmetoxi)-2-(2,4-dichlorophenyl)ethyl]-1H-1,2,4-triazole
1-[2-(2,4-dichlorophenyl)]-2-({4-[(2-phenyl)-2H-tetrazole]benzyl}oxy)ethyl]-4H-1,2,4-triazole
1-{2-[(4'-clorobifenil-4-yl)methoxy]-2-(2,4-dichlorophenyl)ethyl}-4H-1,2,4-triazole
1-[2-(biphenyl-4-ilmetoxi)-2-(2,4-dichlorophenyl)ethyl]-4H-1,2,4-triazole
1-[2-(4-chlorophenyl)-2-{[4-(trifluoromethyl)benzyl]oxy}ethyl]-1H-imidazole
1-[2-(4-chlorophenyl)-2-{[4-(trichloromethyl)benzyl]oxy}ethyl]-1H-imidazole
1-[2-(4-chlorophenyl)-2-{[4-(trifluoromethyl)benzyl]oxy}ethyl]-4H-1,2,4-triazole
1-[2-(4-chlorophenyl)-2-{[4-(trichloromethyl)benzyl]oxy}ethyl]-4H-1,2,4-triazole
1-[2-(2-chlorophenyl)-2-{[4-(trifluoromethyl)benzyl]oxy}ethyl]-1H-imidazole
1-[2-(2-chlorophenyl)-2-{[4-(trichloromethyl)benzyl]oxy}ethyl]-1H-imidazole
1-[2-(2-chlorophenyl)-2-{[4-(trifluoromethyl)benzyl]oxy}ethyl]-4H-1,2,4-triazole
1-[2-(2-chlorophenyl)-2-{[4-(trichloromethyl)benzyl]oxy}ethyl]-4H-1,2,4-triazole
1-[2-(4-fluorophenyl)-2-{[2-(trifluoromethyl)benzyl]oxy}ethyl]-1H-imidazole
1-[2-(4-fluorophenyl)-2-{[2-(trichloromethyl)benzyl]oxy}ethyl]-1H-imidazole
1-[2-(4-fluorophenyl)-2-{[2-(trifluoromethyl)benzyl]oxy}ethyl]-4H-1,2,4-triazole
1-[2-(4-fluorophenyl)-2-{[2-(trichloromethyl)benzyl]oxy}ethyl]-4H-1,2,4-triazole
1-[2-(2,4-difluorophenyl)-2-{[2-(trifluoromethyl)benzyl]oxy}ethyl]-1H-imidazole
1-[2-(2,4-difluorophenyl)-2-{[2-(trichloromethyl)benzyl]oxy}ethyl]-1H-imidazole
1-[2-(2,4-difluorophenyl)-2-{[2-(trifluoromethyl)benzyl]oxy}ethyl]-4H-1,2,4-triazole
1-[2-(2,4-difluorophenyl)-2-{[2-(trichloromethyl)benzyl]oxy}ethyl]-4H-1,2,4-triazole or their salts, solvates, pro-drugs, esters, enantiomers and/or pharmaceutically acceptable diastereoisomers.

Advantageously, the aralkyl benzyl ethers compounds of formula (I) according to the present invention can be prepared by means of an O-alkylation reaction of the correspondent alcohol of the compound to be prepared. The intermediate used for the addition of the alkyl group according to the reaction of O-alkylation of this invention can be, for example, derived from a benzyl halide, benzyl mesylate or benzyl tosylate substituted with groups described later in $R_6$ that are correspondent to the compounds to be prepared.

Reactions may occur in the reaction medium comprising the solvent tetrahydrofuran (THF) and sodium hydride in a concentration range varying from 40% to 80% (w/v) in relation to the total volume of the reaction medium.

In another aspect, the reactions may occur in a reaction medium comprising a polar solvent solution of a strong base in concentrations ranging from 20% to 70% (w/v) and a basic organic salt in concentration ranging from 0.001 to 0.1 g/mL regarding the total volume of the reaction medium. Preferentially, said polar organic solvent may be acetone or methyl ethyl ketone or mixture thereof; said strong base solution can be a base comprising alkali metal and alkaline earth metal elements preferably selected from the group consisting of: sodium hydroxide and potassium hydroxide; said basic organic salt is preferably Triethylaluminium ammonium benzyl chloride.

The intermediates of the reaction may optionally have protecting groups of reactive species, as for example, bond to the reactive nitrogen of the tetrazole ring in intermediates containing it.

Examples of protecting groups may be, but are not limited to: Trityl group, N,N-dimethylsulfonamide, p-metoxiphenylsulfonamide, Benzenesulphonamide, 2,2,2-trichloroethylcarbamate, t-butylcarbamate, N-2-chloroethylamine, N-triisopropylsilylamine, N-2-nitrobenzylamine and/or N-2-tetrahydropyranylamine.

Said preparation process can be generally represented by the following procedure 1:

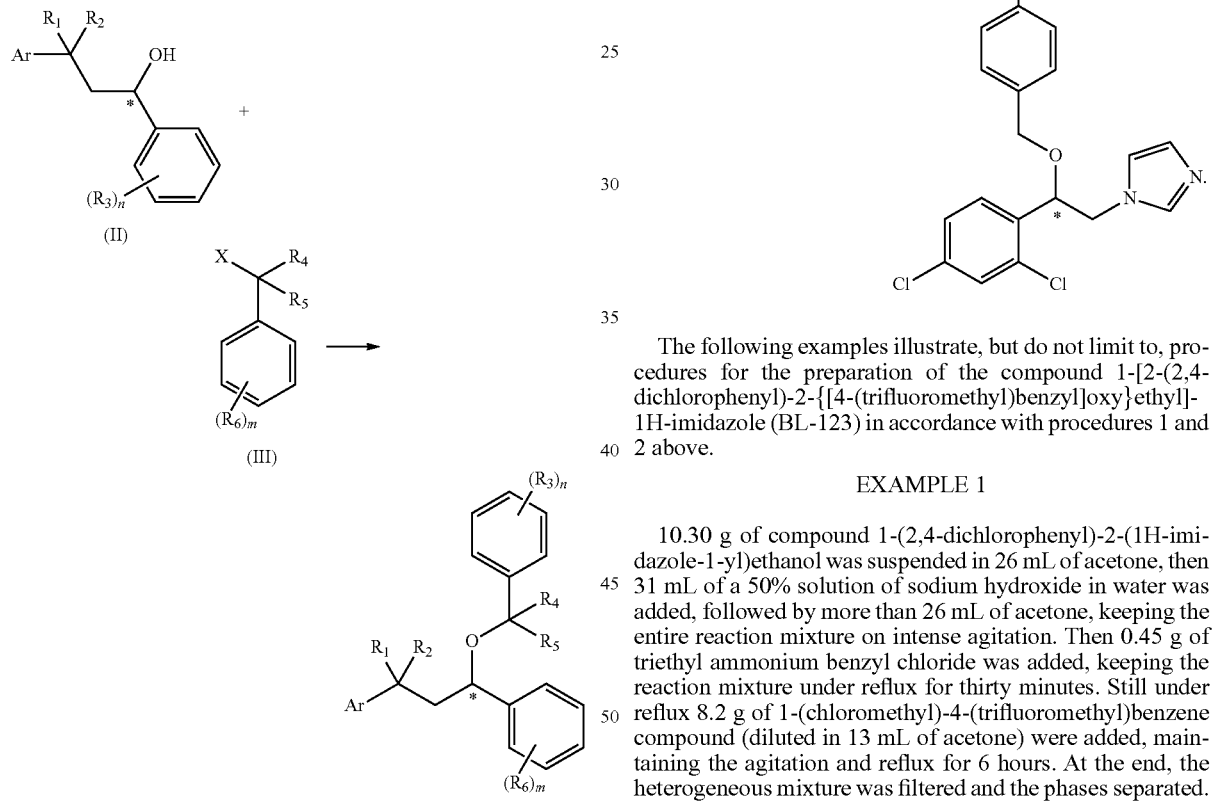

wherein Ar, $R_1$-$R_6$, n and m of formulas (II) and (III) are as defined in the detailed description of formula (I), and wherein X refers to elements selected from the group consisting of Cl, Br, I, MS (methanesulfonates) and TS (toluenesulfonates).

Procedure 1

Advantageously, the derivative 1-[2-(2,4-dichlorophenyl)-2-{[4-(trifluoromethyl)benzyl]oxy}ethyl]-1H-imidazole (BL-123), according to this invention can be prepared from 1-(2,4-dichlorophenyl)-2-(1H-imidazole-1-yl) ethanol and 1-(chloromethyl)-4-(trifluoromethyl)benzene accord ng to the reaction below (Procedure 2).

(Procedure 2)

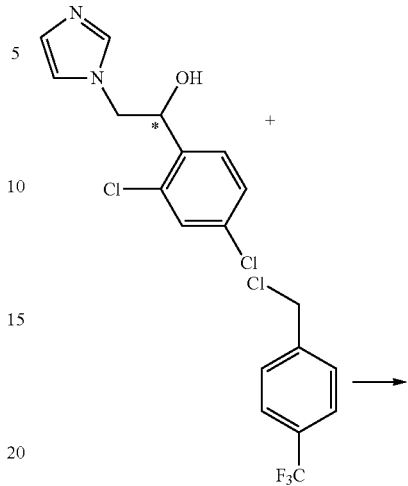

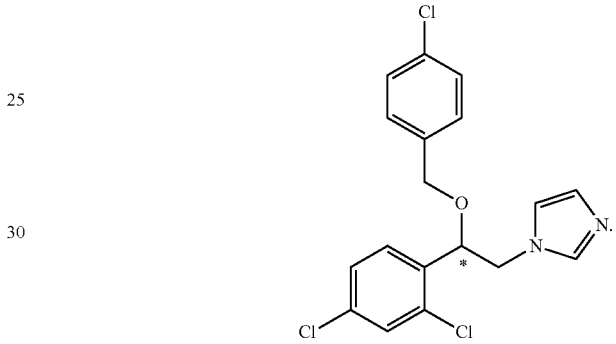

The following examples illustrate, but do not limit to, procedures for the preparation of the compound 1-[2-(2,4-dichlorophenyl)-2-{[4-(trifluoromethyl)benzyl]oxy}ethyl]-1H-imidazole (BL-123) in accordance with procedures 1 and 2 above.

EXAMPLE 1

10.30 g of compound 1-(2,4-dichlorophenyl)-2-(1H-imidazole-1-yl)ethanol was suspended in 26 mL of acetone, then 31 mL of a 50% solution of sodium hydroxide in water was added, followed by more than 26 mL of acetone, keeping the entire reaction mixture on intense agitation. Then 0.45 g of triethyl ammonium benzyl chloride was added, keeping the reaction mixture under reflux for thirty minutes. Still under reflux 8.2 g of 1-(chloromethyl)-4-(trifluoromethyl)benzene compound (diluted in 13 mL of acetone) were added, maintaining the agitation and reflux for 6 hours. At the end, the heterogeneous mixture was filtered and the phases separated. The organic phase was rotoevaporated at 45° C. to dryness. The obtained residue was dissolved in 100 mL of cold ethyl ether. It was then added 2 mL of nitric acid (65%) at 0° C., maintaining the agitation for one hour. At the end the product was filtered and washed with cold ethanol and dried at 65° C. for 12 hours. The product obtained as a white colored solid (compound BL123) had the following characteristics: NMR 1H (300 MHz-DMSO): 9.05 (1H, s), 7.72-7.74 (1H, m), 7.65-7.66 (4H, m), 7.53-7.54 (1H, m), 7.38-7.45 (3H, m), 5.51-5.20 (1H, m) 4.45-4.64 (4H, m). NMR 13C (75 MHz-DMSO): 142.1, 136.3, 134.1, 133.6, 133.3, 129.5, 129.2, 128.5, 128.1, 127.9, 125, 2, 125.1, 123, 119.8, 75.4, 69.7, 51.8; Elementary Analysis calc. for $C_{19}H_{16}Cl_2O_4$, $F_3N_3$: C=47.72%, H=3.37%, N=8.79%; obtained: C=48.06%, H=3.44%, N=8.76%. Melting point: 173-176° C.

EXAMPLE 2

Over a 60% suspension of NaH (2.0 g) in dried tetrahydrofuran (THF) (18 ml) a solution of the compound 1-(2,4-dichlorophenyl)-2-(1H-imidazole-1-ylethanol (5.14 g) in dry THF (52 mL) was added at room temperature. Then, on the reaction mixture it was slowly added a solution containing the compound 1-(chloromethyl)-4-(trifluoromethyl)benzene (3.6 mL) in dry THF (10 mL), keeping the resulting mixture under reflux for three hours. At the end of this period, 50 mL of water was added and the product was extracted with ethyl acetate and dried with magnesium sulfate, and the final solvent was rotoevaporated. The residue obtained after complete evaporation of the solvent was dissolved in diethyl ether (20 mL) and cooled to 0° C. On the solution of the residue, 65% nitric acid (1.4 mL) was, gently, added. Then the product was filtered and dried at 65° C. The pure product was obtained after recrystallization in methanol. The product obtained as a white colored solid (compound BL123) had the following characteristics: 1H NMR (300 MHz-DMSO): 9.05 (1H, s), 7.72 to 7.74 (1H, m), 7.65 to 7.66 (4H, m), 7.53 to 7.54 (1H, m), 7.38 to 7.45 (3H, m), 5.51 to 5.20 (1H, m), 4.45 to 4.64 (4H, m). 13C NMR (75 MHz-DMSO): 13C NMR (75 MHz-DMSO): 142.1, 136.3, 134.1, 133.6, 133.3, 129.5, 129.2, 128.5, 128.1, 127.9, 125, 2, 125.1, 123, 119.8, 75.4, 69.7, 51.8. Melting point: 173 to 176° C.

Advantageously, the derivative 1-[2-(2,4-dichlorophenyl)]-2-({4-[(2-phenyl)-2H-tetrazole]benzyl}oxy)ethyl]-1H-imidazole (BL-137), according to the present invention can be prepared from 1-(2,4-dichlorophenyl)-2-(1H-imidazole-1-yl)ethanol[1] and 5-(4'-(bromomethyl)biphenyl-3-a)-1-Trityl-1H-tetrazole[2] according to the reaction below (Procedure 3).

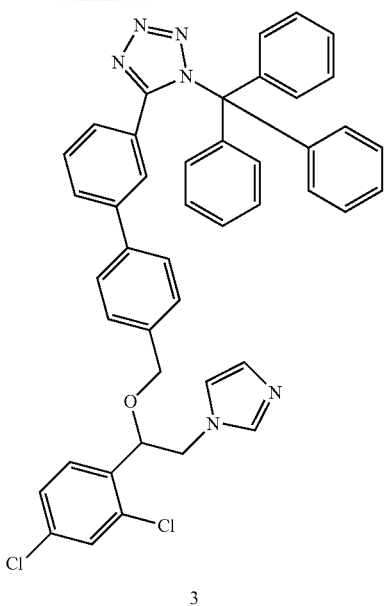

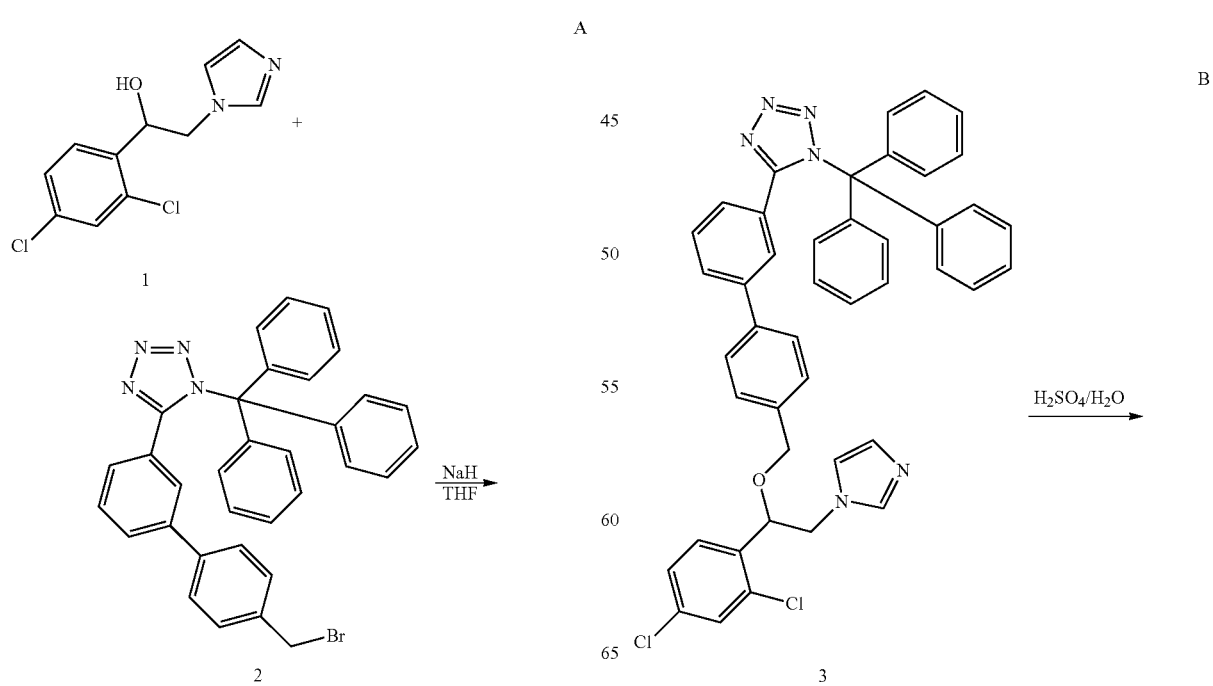

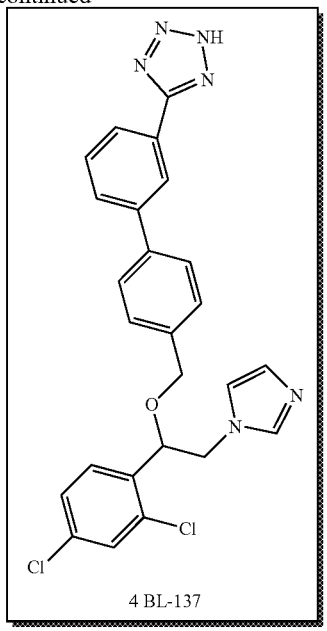

4 BL-137

The following example illustrates, but do not limit to, the preparation of the nitrate compound 1-[2-(2,4-dichlorophenyl)]-2-({4-[(2-phenyl)-2H-tetrazole]benzyl}oxy)ethyl]-1H-imidazole (BL-137) according to procedures 1 and 3 above.

EXAMPLE 3

A 3-way flask equipped with mechanical agitation and reflux condenser was charged with THF (120 mL) and NaH 60% (24 g). To this suspension a solution of 1-(2,4-dichlorophenyl)-2-(1H-imidazole-1-yl)ethanol[1] (0.233 mmol, 60 g in 600 mL of THF) was slowly added and the resulting solution was left under mechanical stirring for 30 min. After this period, the reaction mixture was cooled in an ice bath and to it a solution of 5-(4'-(bromomethyl)biphenyl-3-a)-1-Trityl-1H-tetrazole[2] (0.223 mmol; 129 g in 650 mL of THF) was slowly added. The addition process being completed, the ice bath was removed and the reaction was brought to reflux for 4 hours. After this period, the reaction mixture was cooled to room temperature and to it 560 mL of water were slowly added. This reaction mixture was extracted with 600 mL of ethyl acetate. The organic phase was separated and extracted with a 5% citric acid (2×420 mL) aqueous solution. The aqueous phases were combined and extracted with ethyl acetate (2×300 mL). The organic phases were combined, dried with $MgSO_4$. The solvent was rotoevaporated and an orange oil was isolated.

The crude reaction obtained in step A was dissolved at 50° C. in 1650 mL of acetonitrile. After achieving room temperature, 1300 mL of aqueous $H_2SO_4$ 1.5N were added. This mixture was kept under magnetic stirring for 2 hours. After that, a 2M aqueous solution of NaOH was added, until a pH of 13 was reached. Using vacuum, the reaction mixture was distilled at 65/70° C. in order to remove the acetonitrile. The material remaining in the starting flask was under agitation for 30 min at 30/35° C. The formed precipitate was filtered and washed with 600 mL of a mixture of water/acetonitrile (80/20). The filtrate was extracted with hot toluene (4×450 mL). The aqueous phase was selected and under heating, a sufficient volume of acetic acid was added to turn the pH to around 7.0. Keeping the temperature around 55° C., ethyl acetate was added. This mixture was heated and stirred for 30 min. The organic phase was selected and the aqueous phase was extracted with hot ethyl acetate (3×500 mL). The organic phases were combined and dried with $MgSO_4$. The solvent was removed with a rotoevaporator until the formation of a dense solid occurred. The crude reaction was cooled with an ice bath under mechanical stirring for 2 hours. The precipitate was filtered and washed with 120 mL of acetonitrile. The solid product obtained as a yellowish-white color, compound BL137, had the following characteristics: $RMN^1H$ (300 MHz-$CDCl_3$): 3.78 (1H, dd, J=9 and 15 Hz), 3.91 (1H, d, J=15 Hz), 4.08 (1H, dd, J=3 and 15 Hz), 4.67 (1H, d, J=15 Hz), 4.92 (1H, dd, J=3:09 Hz), 6.78 to 6.86 (2H, m), 6.96 to 7.04 (4H, m), 7.39 to 7.67 (8H, m), 7.98 to 8.01 (1H, m). $RMN^{13}C$ (125 MHz-$CDCl_3$): 52.2, 72.4, 76.8, 119.9, 124.8, 126.4, 128.0, 128.2, 128.6, 128.9; 129.6, 130.6, 130.7, 131.4, 133.1, 134.4, 135.1, 136.1, 136.9, 139.9, 140.7, 155.8. HRMS calc. for $C_{25}H_{20}Cl_2N_6O$ (MH+) m/z 491.1154, obtained 491.1134; Melting point: 93-96° C.

Thus, the compounds described in this invention can be prepared based on any of the procedures 1 to 3, and any of the teachings of the examples 1 to 3, using the corresponding intermediate compounds. For purposes of exemplifying, but not to limit, some intermediate compounds are presented in table 1:

TABLE 1

| | | R1 = | | | | |
| | | R2 = | | | | |
| | | R4 = | | | | |
| Ar | $R_5$ | $(R_3)_n$ | R6 | m | Intermediate I | Intermediate II |
| imidazole | H | 2,4(Cl)$_2$ | para-(3-methylphenyl)tetrazole | 1 | biphenyl-tetrazole-Prot | imidazole-CH$_2$-CH(OH)-dichlorophenyl; X |

TABLE 1-continued

| Ar | R1 = R2 = R4 = R5 | (R3)n | R6 | m | Intermediate I | Intermediate II |
|---|---|---|---|---|---|---|
| 1-methylimidazole | H | 2,4-(Cl)2 | para- 4-Cl-phenyl | 1 | 4'-Cl-biphenyl-CH2-X | 1-(imidazol-1-yl)-2-(2,4-dichlorophenyl)-2-hydroxyethyl |
| 1-methylimidazole | H | H | para- CF3 | 1 | 4-CF3-phenyl-CH2-X | 1-(imidazol-1-yl)-2-phenyl-2-hydroxyethyl |
| 1-methyl-1,2,4-triazole | H | 2,4-(Cl)2 | para- 3-(2H-tetrazol-5-yl)phenyl | 1 | 3-(tetrazol-5-yl-Prot)-biphenyl-CH2-X | 1-(1,2,4-triazol-1-yl)-2-phenyl-2-hydroxyethyl |
| 1-methyl-1,2,4-triazole | H | 2,4-(Cl)2 | para- 4-Cl-phenyl | 1 | 4'-Cl-biphenyl-CH2-X | 1-(1,2,4-triazol-1-yl)-2-(2,4-dichlorophenyl)-2-hydroxyethyl |

TABLE 1-continued

| Ar | R1 = R2 = R4 = R5 | (R3)n | R6 | m | Intermediate I | Intermediate II |
|---|---|---|---|---|---|---|
| [1,2,4-triazole] | H | H | para- CF$_3$ | 1 | [CF$_3$-phenyl-CH$_2$-X] | [triazole-CH$_2$-CH(OH)-(2-Cl,4-Cl-phenyl)] |
| [1,2,4-triazole] | H | 2.4(Cl)$_2$ | para- CF$_3$ | 1 | [CF$_3$-phenyl-CH$_2$-X] | [triazole-CH$_2$-CH(OH)-phenyl] |

Wherein the term "prot" represent the protection groups defined in this invention and "X" represents elements selected from the group consisting of Cl, Br, I, MS (methanesulfonate) and TS (toluenesulfonates).

The compounds of the present invention, as well as their salts, solvates, pro-drugs, esters, enantiomers and/or pharmaceutically acceptable diastereoisomers, potentially have antimicrobial activity, preferably antifungal activity.

Particularly, the compounds described in this invention, and the pharmaceutically acceptable salts thereof can be used as antifungal agents the same being fungicides and/or fungistatics. The fungicides are antifungal agents that destroy the integrity and/or operation of the fungal cell stimulating their death, while the fungistatic antifungals are agents with the ability to prevent growth and/or cell division of fungi making them static. Interestingly, fungicide agents have the potential to clear the fungal infection of the host, and fungistatic agents usually do not completely eliminate the infection.

In addition, the compounds described in the present invention are useful as inhibitors and/or retardants of the proliferation and/or survival of microorganisms such as fungi, bacteria and/or protozoa, particularly of pathogenic microorganisms.

Fungi can be parasites of almost every group of eukaryotic organisms from single-cell organisms such as algae and protozoa, to complex plants, animals and man himself. Microorganisms such as fungi that cause disease and/or disorders in plants and/or animals are called pathogens, more specifically pathogenic microorganisms. It is understood by disease, condition and/or disorder, an abnormal condition of an organism that impairs one or more body functions, associated with specific symptoms and signs, which may be caused by external factors, such as invading organisms, or by intrinsic factors of the organism. The diseases clinically evident as a pathological state resulting from the invasion of the body by pathogenic microorganisms such as viruses, bacteria, fungi, protozoa, multicellular parasites and proteins known as prions, are named infections.

Fungi that are pathogenic to mammals can be divided into three morphological types: (a) yeasts, which are unicellular and reproduce asexually growing in the form of colonies, (b) filamentous fungi, which are multicellular, have septate or aseptic hyphae, can reproduce sexually, asexually or parassexually, and (iii) dimorphic, which may exist in yeast or filamentous form, depending on temperature and environmental conditions. The filamentous fungi can be classified into: (i) dermatophytes, and (ii) anemophilous.

Particularly, the compounds described in the present invention, their salts and solvates, pro-drugs, esters, enantiomers and/or pharmaceutically acceptable diastereoisomers can be used in the treatment and/or prevention of primary pathogenic fungi that can be represented, but are not limited to, dermatophyte fungi and dimorphic fungi. It is understood by treatment a set of means, such as pharmacological, surgical or physical whose purpose is the cure or relief of diseases or symptoms, after making a diagnosis. While prevention is the use of means to prevent the onset of an illness or symptom and/or its spreading.

The main types of medically relevant dermatophytes are *Epidermophyton* sp, *Trycophyton* sp and *Microsporum* sp among which, the following species may be highlighted: *Trichophyton mentagrophytes, Trichophyton verrucosum, Trichophyton rubrum, Trichophyton shoenleinii, Trichophyton tonsurans, Trichophyton violaceum, Trichophyton concentricum, Microsporum gypseum, Microsporum canis, Microsporum audouinii* and *Epidermophyton floccosum*.

Among the dimorphic fungi, the main species of medically important fungi are: *Paracoccidioides brasiliensis, Histoplasma capsulatum, Blastomyces dermatiditis, Coccidioides immitis, Penicillium marneffei*, and *Sporothrix schenckii*.

The anti-fungal activity of the compounds of this invention was measured using the in vitro analysis of minimum inhibitory concentration (MIC) of compound 1-[2-(2,4-chlorophenyl)-2-{[4-(trifluoromethyl)benzyl]oxy}ethyl]-1H-imidazole (BL-123).

The antifungal activity of the compound BL-123 was tested in several strains of filamentous dermatophyte fungi from clinical and laboratory isolates, as shown in example 4.

EXAMPLE 4

4.1 Cultivation of Fungal Strains

For the experiments of the present invention, the dermatophyte-type fungi strains that were obtained from clinical isolates and laboratory isolates, as described in Table 2 as follows, were used:

TABLE 2

| No. | Identification | Name |
|---|---|---|
| Strains obtained from clinical isolates | | |
| I. | 16404 | *Aspergillus Niger* |
| II. | 2 | *Trichophyton mentagrophytes* |
| III. | 24 | *Microsporum gypseum* |
| IV. | 381a | *Trichophyton verrucosum* |
| V. | 28188 | *Trichophyton rubrum* |
| VI. | 373 | *Microsporum canis* |
| VII. | 381b | *Trichophyton verrucosum* |
| VIII. | 455 | *Trichophyton rubrum* |
| Laboratory strains of isolates obtained | | |
| IX. | 22019 | *Candida parapsilosis* |
| X. | 40004 | *Trichophyton mentagrophytes* |
| XI. | 40005 | *Trichophyton rubrum* |
| XII. | 40051 | *Microsporum gypseum* |
| XIII. | 9533 | *Trichophyton mentagrophytes* |

The fungal strains were grown on agar potato medium in a sloping chute at a temperature of 30° C. for a period of 7 to 15 days.

4.2 Mounting of Preparations and Test

For the experiments, the compound 1-[2-(2,4-dichlorophenyl)-2-{[4-(trifluoromethyl)benzyl]oxy}ethyl]-1H-imidazole (BL-123) in the form of its nitrate salt and miconazole nitrate were used. Both compounds were dissolved in dimethyl sulfoxide (DMSO) to match the final concentration of the compound equal to or less than 1%.

The methodology used to test the sensitivity of the agent was of broth microdilution according to the method described in Standard M38-A (Reference method for broth dilution tests for determining the sensitivity to antifungal therapy for filamentous fungi; NCCLS, volume 22 No. 16, USA, 2008) as follows.

The fungus was cultivated pursuant to item 4.1. To the tubes wherein the fungi were grown, 5 mL of saline solution were added in order to extract the fungi from the agar surface. Then, this homogeneous suspension was transferred to a new tube and the colony-forming units (CFUs) were quantified according to counting methods: (i) in Sabouraud dextrose agar plates and (ii) in a Neubauer chamber.

Then, the fungi strains listed in Table 2 were inoculated in duplicate in a 96-well plate. There were used inocula of from 2 to $6 \times 10^3$ CFU/mL of fungi, per well, in a total volume of 0.2 mL of RPMI-1640 (containing L-glutamine and without bicarbonate) buffered at pH 7.0 with MOPS (acid 3-(N-morpholine) 15 propanesulfonic). The procedure was performed in a laminar flow.

The compounds to be tested were added in a serial dilution, in duplicate, in final concentrations of 16 µg/mL; 8 µg/mL; 4 µg/mL; 2 µg/mL; 1 µg/mL; 0.5 µg/mL; 0.25 µg/mL; 0.125 µg/mL; 0.0625 µg/mL; or 0.03125 µg/mL in culture medium present in each well.

The incubation of fungi with these compounds was performed by 4, 5, 6 and 7 days at temperatures from 30 to 35° C.

The fungi quantification was carried out with the growth of fungi in each well being compared to the growth occurred in the negative control by means of a mirror reading. The negative control is represented by fungi grown in culture medium in the absence of the tested compounds. The methodology of this comparison is the numerical rating to which the microdilution well was submitted. In this methodology, value 4 corresponds to no reduction of growth, value 3 corresponds to a slight reduction in growth or approximately 75% of the growth of the negative control, value 2 corresponds to a standout reduction in growth or approximately 50% of growth of negative control; value 1 corresponds to a slight growth or approximately 25% of the growth of the negative control, and value 0 corresponds to optically clear or absence of growth.

In this experiment, the minimum inhibitory concentration (MIC) is considered as the lowest concentration of the agent capable of inhibiting at least 80% of the growth of colony-forming units (CFUs).

The results obtained in said experiment are shown in Table 3, which describes the average MIC achieved in four independent experiments considering 4 and 7 days of incubation with the compound BL123 or miconazole.

The compound of the present invention, BL123, showed that it exerts an inhibitory effect on growth of 13 different strains corresponding to seven different species of the dermatophyte kind fungi.

Interestingly, the results shown in Table 3 show that some strains of clinical isolates that are resistant to miconazole (strains I, VII and VIII) are otherwise sensitive to the action of the compound BL-123.

TABLE 3

(Average of MICs performed on different days with readings in the fourth and seventh days.)

| | | | Miconazole (µg/mL) | | BL-123 (µg/mL) | |
|---|---|---|---|---|---|---|
| | Strains | Microorganism | Day 4 | Day 7 | Day 4 | Day 7 |
| I | 16404 | *Aspergillus Niger* | >16 | >16 | 8 | 8 |
| II | 2 | *Trichophyton mentagrophytes* | 1 | 1 | 4 | 4 |
| III | 24 | *Microsporum gypseum* | 0.05 | 0.05 | 0.25 | 0.25 |
| IV | 381 | *Trichophyton verrucosum* | >16 | >16 | >16 | >16 |
| V | 28188 | *Trichophyton rubrum* | 0.03 | 0.06 | 0.03 | 0.03 |
| VI | 373 | *Microsporum canis* | 0.5 | 1 | 0.125 | 0.5 |
| VII | 381 | *Trichophyton verrucosum* | >16 | >16 | 4 | >16 |
| VIII | 455 | *Trichophyton rubrum* | >16 | >16 | 4 | 8 |
| IX | 22019 | *Candida parapsilosis* | 1 | — | 2 | — |
| X | 40004 | *Trichophyton mentagrophytes* | 0.5 | 1 | 0.25 | 0.5 |
| XI | 40005 | *Trichophyton rubrum* | 0.5 | 1 | 0.25 | 0.5 |
| XII | 40051 | *Microsporum gypseum* | 0.03 | 0.06 | 0.03 | 0.03 |
| XIII | 9533 | *Trichophyton mentagrophytes* | 0.06 | 0.125 | 0.03 | 0.125 |

The inhibitory effect of the compound BL123 was corroborated by the results obtained in experiments aimed at obtaining the values of minimum inhibitory concentration to inhibit 50% of the tested isolates ($MIC_{50}$) the minimum inhibitory concentration to inhibit 90% of the isolates tested ($MIC_{90}$) and the variation of MICs (VMIC) as described in Table 4.

In these experiments, we found that the inhibitory effect of BL123 remained the same when we used low concentrations of the compound in order to inhibit the growth of 90% of the population of the strains tested. In contrast, a majority of the population of the same strains when treated with miconazole proved unresponsive to treatment when used at the lowest concentration that inhibits the growth of 50% of the population.

TABLE 4

(Values average of $MIC_{50}$ and $MIC_{90}$ and variation of MICs for the agents tested)

| | Miconazole Average MIC (µg/mL) | | BL-123 Average MIC (µg/mL) | |
|---|---|---|---|---|
| n = 13 | Day 4 | Day 7 | Day 4 | Day 7 |
| MIC50 | 0.5 | 1 | 0.25 | 0.5 |
| MIC90 | >16 | >16 | 4 | 8 |
| VMIC | 0.03->16 | 0.06->16 | 0.03->16 | 0.03->16 |

The antimicrobial activity of compounds of the present invention was measured using the in vitro analysis of minimum inhibitory concentration (MIC) of compounds 1-[2-(2,4-dichlorophenyl)-2-{[4-(trifluoromethyl)benzyl]oxy}ethyl]-1H-imidazole (BL-123) and 1-[2-(2,4-dichlorophenyl)]-2-({4-[(2-phenyl)-2H-tetrazole]benzyl}oxy)ethyl]-1H-imidazole (BL-137).

The antimicrobial activity of compounds BL-123 and BL137 was tested in several strains of yeast-like fungi and bacteria, as shown in Example 5.

EXAMPLE 5

5.1 Cultivation of Yeast Strains and Bacteria

For the experiments of the present invention (i) yeast strains obtained from clinical isolates and laboratory isolates, and (ii) bacterial strains obtained from laboratory isolates were used, as described in Table 5 as follows.

TABLE 5

(yeast and bacteria strains used in the test)

| No. | Identification | Name |
|---|---|---|
| Yeast strains-isolated laboratory | | |
| XIV. | 10231 | *Candida albicans* |
| Yeast strains-Clinical Isolates | | |
| XV. | 22019 | *Candida parapsilosis* |
| XVI. | 2001 | *Candida glabrata* |
| Bacteria strains-isolated laboratory | | |
| XVII. | 12228 | *Staphylococcus epidermidis* |
| XVIII. | 6538 | *Staphylococcus aureus* |

5.1.a Cultivation of Yeast Strains-Preparation of Inoculum

The yeast strains were grown in culture medium Sabouraud Dextrose Agar maintained at a temperature of 35° C. for 48 hours.

5.1.a Cultivation of Bacteria Strains-Preparation of Inoculum

The bacterial strains were grown in culture medium Triptic Soy Agar at 35° C. for two to six hours (or until the turbidity of a McFarland standard solution equal to 0.5). 5.2 Mounting of Preparations and Test For the experiments, compound 1-[2-(2,4-dichlorophenyl)-2-{[4-(trifluoromethyl)benzyl]oxy}ethyl]-1H-imidazole (BL-123) in the form of its nitrate salt, 1-[2-(2,4-dichlorophenyl)]-2-({4-[(2-phenyl)-2H-tetrazole]benzyl}oxy)ethyl]-1H-imidazole (BL-137), and miconazole nitrate were used. The compounds were dissolved in dimethyl sulfoxide (DMSO) to match the final concentration of the compound equal to or less than 1%.

5.2.a Yeast Strains

The methodology used to test the sensitivity of the agent was broth microdilution according to the method described in Standard M27-A2 (Reference method for broth dilution tests to determine the sensitivity of yeasts to antifungal therapy-second edition, NCCLS, volume 22 number 15, USA, 2002) as follows.

The yeast strains were grown according to item 5.1.a to obtain a culture containing between $1 \times 10^6$ and $5 \times 10^6$ CFU/mL. Then the suspensions were diluted in culture medium RPMI-1640 (buffered with MOPS 0.165 mol/l) at a final concentration of 50 to 2500 CFU/mL.

The diluted suspensions were inoculated in duplicate in a 96-well plate. The procedure was performed in a laminar flow.

The compounds to be tested were added in a serial dilution, in duplicate, in final concentrations of 16 µg/mL; 8 µg/mL; 4 µg/mL; 2 µg/mL; 1 µg/mL; 0.5 µg/mL; 0.25 µg/mL; 0.125 µg/mL; 0.0625 µg/mL; or 0.03125 µg/mL in culture medium present in each well. The incubation of fungi with these compounds was carried out for 48 hours at temperature of 30 to 35° C.

5.2.b Cultivation of Bacterial Strains

The methodology used to test the sensitivity of the agent was broth microdilution according to the method described in Standard M7-A6 (Methodology of sensitivity tests to antimicrobial agents by dilution for bacteria with aerobic growth—6th Edition: NCCLS, volume 23, No. 2, USA, 2003), as follows.

The bacterial strains were grown according to item 5.1.b in order to obtain a culture containing between $1 \times 10^7$ and $5 \times 10^7$ CFU/mL. Then the suspensions were diluted in Mueller Hinton culture medium to a final concentration of $5 \times 10^4$ CFU/mL.

The diluted suspensions were inoculated in 0.1 mL in duplicates in 24-well plates. The procedure was performed in a laminar flow.

The compounds to be tested were added in a serial dilution, in duplicate, in final concentrations of 16 µg/mL; 8 µg/mL; 4 µg/mL; 2 µg/mL; 1 µg/mL; 0.5 µg/mL; 0.25 µg/mL; 0.125 µg/mL; 0.0625 µg/mL; or 0.03125 µg/mL in 0.9 mL of culture medium present in each hole.

Incubation of fungi with these compounds was carried out for 24 hours at a temperature of 30 to 35° C.

After incubation, microbial growth was observed with naked eye in relation to the turbidity or presence of deposit in the bottom of the chute. We have agreed in this experiment that the turbid medium is the result of microbial growth and the presence of deposit and a clear medium represents the absence of microbial growth. The minimum inhibitory concentration (MIC) was defined as the lowest tested drug concentration that prevents any degree of bacterial growth.

The compounds of the present invention BL123 and BL137 showed that they exert an inhibitory effect on the growth of three different species of yeast and two distinct species of bacteria as shown in Table 6 below.

TABLE 6

(MICs for strains of yeasts and bacteria)

| | Strains | Microorganism | Miconazole (μg/mL) | BL-123 | BL-137 |
|---|---|---|---|---|---|
| XIV. | 10231 | Candida albicans | 4.0 | 8.0 | 512.0 |
| XV. | 22019 | Candida parapsilosis | 2.0 | 4.0 | 512.0 |
| XVI. | 2001 | Candida glabrata | 0.125 | 0.125 | 512.0 |
| XVII. | 12228 | Staphylococcus epidermidis | 2.0 | 4.0 | 128.0 |
| XVIII. | 6538 | Staphylococcus aureus | 2.0 | 4.0 | 128.0 |

From the observed in this experiment we concluded that the compounds of the present invention have an inhibitory effect on the growth of microorganisms, and therefore can be used as antimicrobials, preferably against fungi and bacteria. It is understood to be an antimicrobial any agent being a chemical that destroys or inhibits the growth of microorganisms such as fungi, bacteria and/or protozoa, or that has the ability to destroy viruses.

Examples of fungi against which the compounds of this invention are intended may be, but are not be limited to, the genera: *Aspergilus, Microsporum, Epidermophyton, Trichophyton, Candida, Phycomyces, Zygomyces, Rhizopus, Mucor, Absidia, Malassezia, Exophiala, Piedraia, Trichosporum, Sporothrix, Cladosporium, Phialophora, Fosecaea, Histoplasma, Coccidioides, Fusarium, Penicillium, Blastomyces, Cryptococcus, Paracoccidioides, Scedosporium, Sacharomyces, Piedraia, Actinomyces, Keratinomyces, Nannizia, Arthroderma, Ctenomyces, Olpidium, Physodema, Synchytrium, Phytophora, Verticillium, Gliocladium, Rhytisma, Sclerotinia, Ophiostoma, Lophiodermium, Elsinoe, Capnodium, Mycosphaerella, Venturia, Gaeumannomyces, Alternaria, Bipolaris, Botrytis, Cercospora, Diplodia, Dreschlera, Exerohilum, Phoma, Phomopsis, Rhisoctonia, Puccinia, Erysphe, Phyllactinia, Uncinula, Phragmidium, Melampsora, Eutypha, Hypoxylon, Xylaria, Ceratobasidium, Heterobasidium, Thanatephorus, Armillaria*, among others.

Examples of bacteria against which the compounds of this invention are intended can be of the genera *Actinomyces, Corynebacterium, Mycobacterium, Nocardia, Bacillus, Bifidobacterium, Clostridium, Erysipelothrix, Listeria, Staphylococcus, Streptococcus, Pneumococcus, Anaplasma, Ehrlichia, Neorickettsia, Wolbachia, Bacterioides, Bartonella, Bordetella, Borrelia, Brucella, Burkholderia, Campylobacter, Chlamydia, Chlamydophila, Escherichia, Klebsiella, Proteus, Salmonella, Serratia, Yersinia, Fusobacterium, Helicobacter, Acinetobacter, Mycoplasma, Ureaplasma, Neisseria, Meningococcus, Actinobacillus, Haemophilus, Pasteurella, Pseudomonas, Rickettsia, Treponema*, among others.

Examples of protozoa against which the compounds of this invention are intended, may be of the genera: *Plasmodium, Toxoplasma, Balantidium, Coccidia, Cryptosporidium, Cylospora, Isospora, Sarcocystis, Babesia, Theileria, Dientamoeba, Giárdia, Leishmania, Acanthamoeba, Blastocystis, Anaplasma, Ehrlichia, Trychomonas, Trypanosoma, Giardia, Entamoeba*, among others.

The compounds described in the present invention, as well as their salts, solvates, prodrugs, esters, enantiomers and/or pharmaceutically acceptable diastereoisomers, can be used in the manufacture of a drug for the treatment and/or prevention of conditions and/or diseases associated to microorganisms such as fungi, bacteria and/or protozoa. In addition, the compounds described in the present invention, as well as their salts, solvates, pro-drugs, esters, enantiomers and/or pharmaceutically acceptable diastereoisomers can be used in the manufacture of a medicine for inhibiting the proliferation and/or survival of microorganisms, such as fungi, bacteria and/or protozoa, particularly of pathogenic microorganisms.

Thus, the present invention provides a method for the treatment and/or prevention of conditions and/or diseases associated with microorganisms such as fungi, bacteria and/or protozoa, e.g. dermatophytes, yeasts, filamentous non-dermatophyte fungi, Gram-negative and Gram-positive bacteria and protozoa in a mammal by administering at least one compound described in formula (I) of the present invention and their salts, solvates, pro-drugs, esters, enantiomers and/or pharmaceutically acceptable diastereoisomers.

The present invention also provides a method for inhibiting the proliferation and/or survival of microorganisms such as fungi, bacteria and/or protozoa, particularly pathogenic microorganisms.

Therefore, provided the proven effectiveness, we consider the formula (I) compounds and the pharmaceutically acceptable salts thereof to be of interest in therapy, specifically in the treatment and/or prevention of conditions and/or diseases in individuals associated with microorganisms such as fungi, bacteria and/or protozoa. It is understood by individual the body that represents both a totally independent physiological unit and a single genotype.

Diseases that affect men when caused by fungal pathogens are called mycoses. Mycoses can be classified into three groups depending on the location and depth in which they occur in the body, which are: (i) superficial mycoses: infection on the surface of skin, nail, hair mucosa and/or hair, (ii) subcutaneous mycoses, caused by fungi capable of penetrating deep skin layers, such as subcutaneous tissue, connective tissue and bone tissue, and (iii) systemic mycoses (or deep): the most severe fungal infections and invasive that can be acquired by inhalation of spores of pathogenic fungi that remain and grow in the lungs and reach the bloodstream and can infect other internal organs of the body.

The main superficial mycoses are caused by dermatophytes fungi and are called dermatophytosis. Examples of the most common dermatophytosis may be: (i) tinea captis (scalp) caused by various dermatophytes, such as *M. canis* (microsporic tinea captis), *T. tonsurans* (tonsuring tinea), *T. mentagrophytes, E. floccosum, M. gypseum* (Kerion), *T. violaceum, T. schoenleinii* (tinea captis' athlete's foot) *T. verrucosum*, and *T. schonleinii* (tinea combs), (ii) tinea barbae (beard) caused by *T. rubrum* and *T. mentagrophytes* (iii) tinea corporis (skin glaber) most often caused by *T. rubrum, T. mentagrohytes* and *M. kennels*, (iv) tiene pedis (foot and hand), often caused by *T. rubrum, T. mentagrohytes* and *E. floccosum* (v) tinea cruris (groin) caused by *T. rubrum, T. mentagrohytes* and *E. floccosum* (vi) the ear tinea caused by *M. kennels*, (vii) imbricate tinea caused by *T. concentricum* (viii) tinea of the nail (Onychomycosis) caused mainly by various dermatophytes of the genera *Trichophyton, Epidermophyton*, rarely by *Microsporum;*

In addition, fungi that are not naturally pathogenic to humans can develop opportunistic infections, secondary to other pre-existing conditions and debilitating the host immune system. The main examples of fungi that cause opportunistic infections are: (i) filamentous fungi, mostly belonging to the genera *Aspergillus* sp, *Fusarium* sp, *Scedosporium* sp, Mucorales and Dematiaceous and (ii) yeast, mostly belonging to the genera *Candida* sp, *Cryptococcus* sp, *Trichosporon* sp, *Rhodotorula* SP, *Malassezia* sp and *Saccharomyces* sp.

Examples of clinically relevant dermatosis caused by other opportunistic filamentous fungi can be (i) versicolored pityriasis (skin) caused by *Malassezia furfur*; (ii) pityrosporum folliculitis caused by the fungus *Malassezia furfur* infection in pilosebaceous; (iii) tinea nigra (palms of the hands or edges of the fingers), caused by *Cladosporium werneckii* (iv) black piedra (hair) caused by the fungus *Piedraia hortai*.

Additionally, examples of diseases caused by opportunistic fungal yeast can also be cited, such as (i) trichosporonosis caused by the yeast fungus *Trichosporon beigelii* subdivided into white piedra (hair) and genital inguinal trichosporonosis (rash in the genital and groin region), (ii) candidosis caused by *Candida* sp, the most frequent being *C. albicans* but it can be found also found the species *C. tropicalis, C. parapsilosis, C. guilliermondii* and the candidosis can be subdivided into oral candidosis, vulvovaginal candidosis, balanopreputial candidosis, intertriginous candidosis, mucocutaneous candidosis and follicular candidosis.

Among the deep mycoses are: (i) paracoccidioidomycosis caused by *Paracoccicioides brasiliensis*, which is manifested through the tegumental or mucocutaneous forms, lymph nodular forms, Vicere forms and in other organs and mixed forms, (ii) lobomycosis caused by *Paracoccidioides loboi* (iii) chromoblastomycosis or chromomycosis is caused by pigmented fungi such as *Fosecaea pedrosoi, Fosecaea compacta, Cladosporium cartionii, Phialophora verrucosa* and *Rhinocladiella aquaspersa;* (iv) sporotrichosis caused by *Sporothrix schenckii* and manifests itself in extra cutaneous and extra-cutaneous forms, (v) Eumycetoma or maduromycosis, caused by several fungi which include *Pietriellidium boydii, Cephalosporium* sp, *Madurella* sp, *Pyrenochaeta* sp, *Exophiala* sp; (vi) histoplasmosis caused by *Histoplasma capsulatum*, (vii) phaeohyphomycosis caused by fungi *Exophiala jeanselmei, Wangiella dermatitis, Cladosporium bantiasenum, Alternaria alternada, Exophiala moniliae, Exophiala spinifera, Phialophora verrucosa, Phloma* sp, *Curvularia geniculata, Mycelia sterilia*; (viii) entomophthoromycosis caused by the fungi *Basidiobolus haptosporus, Conidiobolus coranatus* or *Conidiobolus incongrus*; (ix) mucormycosis caused by the fungus *Absidia corymbifera, Rhizomucor pussilus, ramossimus Mucor, Rhizopus microsporus, Rhizopus oryzae, Rhizopus rhizopodiformis, Cunninghamella Berthollet, Saksenae vasiformis*; (x) cryptococcosis caused by *Cryptococcus neoformans*; (xi) Coccidioidomycosis caused by *Coccidioides immitis* (xii) North American blastomycosis caused by *Bastomyces dermatitis*, (xiii) Rhinosporidiosis caused by *Rhinosporidium seeberi*.

More particularly, the compounds of formula (I) of this invention can be used, but not limiting, for the treatment or prevention of conditions and/or diseases such as microsporic tinea captis, tinea tonsuring, Kerion, tinea captis' athlete's foot, "broad bean" tinea, tinea barbae, tinea corporis, tinea pedis, tinea cruris, ear tinea, imbricate tinea, nail tinea, versicolored pityriasis, pityrosporum folliculitis, tinea nigra, black piedra, trichosporonosis, oral candidosis, vulvovaginal candidosis, balanopreputial candidosis, intertriginous candidosis, follicular candidosis and/or mucocutaneous candidosis.

The diseases caused by fungi that attack plants have relevance since the parasites are destructive to them, and occur mainly on cultivated plants, which causes extensive damage in agriculture. These diseases can be called rust, mildew, soot or mold, depending on the causative agent, and some fungi can also produce toxins-mycotoxins. Mycotoxins can cause disease in men, such as aflatoxin, produced by *Aspergillus flavus* that are carcinogenic to man.

Examples of conditions and/or diseases associated with bacteria that can be treated and/or prevented by administering the compounds of This invention can be, but not limiting to: actinomycosis, Whiple disease, diphtheria, erythrasma leprosy, Buruli ulcer, paratuberculosis, tuberculosis, tuberculoma, pericarditis, erythema, mycetoma, anthrax, botulism, enterocolitis, enterotoxemia, gas gangrene, tetanus, erysipelas, meningitis, pneumonia, furunculosis, impetigo, endocarditis, rheumatoid fever, anaplasmosis, ehrlichiosis, angiomatosis, brucellosis, melioidosis, conjunctivitis, lymphogranuloma venereum, trachoma, psittacosis, dysentery, granuloma, typhoid fever, paratyphoid fever, gingivitis, legionellosis, leptospirosis, pleuropneumonia, gonorrhea, typhus, paints, syphilis, cancer, neurosyphilis, tularemia, cholera, among others.

Examples of conditions and/or diseases associated with protozoa that can be treated and/or prevented by administering the compounds of this invention can be, but not limiting to: malaria, toxoplasmosis, balantidiasis, coccidoidose, Cryptosporidiosis, cyclosporiasis, isosporiasis, Sarcocystosis, babesiosis, dourine, theileriosis, trypanosomiasis, Dientamoebiasis, giardiasis, leishmaniasis, trichomoniasis, Chagas disease, amoebiasis, dysentery amoeboid, among others.

The compounds described in formula (I) of the present invention and their salts, solvates, prodrugs, esters, enantiomers and/or pharmaceutically acceptable diastereoisomers can be administered by any appropriate means, such as topically, orally, parenterally, intraperitoneally and/or vaginally.

The pharmaceutical compositions comprising as active ingredient an effective amount of the derivatives of formula (I) or its salts, solvates, pro-drugs, esters, enantiomers and/or pharmaceutically acceptable diastereoisomers, alone or in a mixture of at least two compounds of formula (I) of the present invention may be presented as a liquid, semisolid or solid, such as, but not limited to (i) creams, gels, gel-creams, hydrogels, powders, ointments, lotions or emulsions; (ii) capsules optionally coated, chewable, effervescent, multi-layers or soluble; (iii) capsules of any kind, such as gel-like hard capsule, gel-like soft capsule, and starch; (iv) capsules; (v) post-dispersible or effervescent; (vi) tablets; (vii) granules, optionally in the form of microparticles or microcapsules, or in vectorized preparations, such as liposomes; (viii) optionally topical, oral, nasal or ophthalmic solutions; (ix) suppositories; (x) syrups; (xi) suspensions; (xii) injection including subcutaneous, intradermal, intramuscular and intravenous administration, among others.

Also included in the present invention are the pharmaceutical compositions of controlled action, fast action, prolonged action and delayed action.

The pharmaceutical compositions, as well as the drug comprising the compounds described in the present invention, as well as their salts, solvates, pro-drugs, esters, enantiomers and/or pharmaceutically acceptable diastereoisomers are used to treat conditions caused by fungi and/or other microorganisms such as bacteria and/or protozoa in a mammal.

Pharmaceutical compositions comprising as active ingredients the compounds described in the present invention, as well as their salts, solvates, pro-drugs, esters, enantiomers and/or pharmaceutically acceptable diastereoisomers may comprise these compounds alone or in mixtures thereof and in combination with another active ingredient.

For administration to mammals in curative or prophylactic treatment of conditions caused by fungi and/or other microorganisms such as bacteria and/or protozoa, the dosages of the compounds described in formula (I) are comprised in the range from 0.001 to 1000 mg daily for a patient in need thereof. In practice, the physician should determine the most suitable unit doses system for each patient, which varies depending on the age, weight and individual response.

Examples that can illustrate a few topical pharmaceutical formulations comprising the compounds of formula (I) according to the present invention can be, but are not limited to, the ones described below

EXAMPLE 6

TABLE 7

Formulation in the form of antifungal cream

| Description | Quantity for 100 g of product | Unit |
|---|---|---|
| BL-123 | 1.000 | g. |
| Cetyl Alcohol | 6,000 | g. |
| Anhydrous lanolin | 6,000 | g. |
| Isopropyl myristate | 10,000 | g. |
| Propylene glycol monostearate | 4.000 | g. |
| Methylparaben | 0.100 | g. |
| Sorbitan monostearate | 4.000 | g. |
| Propylene glycol | 10,000 | g. |
| Propylparaben | 0.050 | g. |
| Polysorbate 60 | 6,000 | g. |
| FRAGRANCE | 0.00 to 0.50 | g. |
| DMSO (dimethyl sulfoxide) | 0.00 to 5.00 | g. |
| Purified Water QSP | 100.000 | g. |

Procedure:

In a first container, water was heated at 75° C.±5° C. and methylparaben and propylparaben were dissolved. In a second container, anhydrous lanolin, polysorbate 60, sorbitan monostearate, cetyl alcohol, propylene glycol monostearate and the isopropyl myristate were heated to 75° C.±5° C. until complete fusion. The content of the first container was added to the content of the second container under stirring and then cooled to 45° C.±5° C. To this mixture the active BL-123, propylene glycol, and optionally DMSO, were slowly added. The mixture obtained was cooled until the temperature of 30° C. (25-35° C.) and to it a fragrance can optionally be added. The weight was completed with water and the mixture was homogenized.

EXAMPLE 7

TABLE 8

Anti-fungal formulation in powder form

| Description | Quantity for 100 g of product | Unit |
|---|---|---|
| BL-123 | 1.000 | g. |
| Colloidal silicon dioxide | 1.00 | g. |
| ZINC OXIDE | 5.00 | g. |
| FRAGRANCE | 0.00 to 0.50 | g. |
| TALC (PHARM LEVEL.) QSP | 100.00 | g. |

Silicon dioxide and fragrance were mixed and then passed through a 60 mesh sieve. In a separate container, the active BL-123, zinc oxide and pharmaceutical grade talc were mixed and passed through the 40 mesh sieve. After this process, the powders were mixed.

EXAMPLE 8

TABLE 9

Formulation in the form of antifungal lotion

| Description | Quantity for 100 ml of product | Unit |
|---|---|---|
| BL-123 | 1.00 | g. |
| Macrogol 300 | 50.00 | g. |
| FRAGRANCE | 0.00 to 0.50 | g. |
| DMSO (dimethyl sulfoxide) | 0.00 to 5.00 | g. |
| Propylene QSP | 100.00 | mL |

To a container with adequate capacity 300 Macrogol and propylene glycol were added and heated at a temperature of 60° to 70° C. Then, under stirring, the active ingredients BL-123 and, optionally, DMSO were added at a temperature of 60° C.-70° C. and mixed until complete dissolution. The mixture was cooled to 30° C. and optionally you can add a fragrance. The final volume was completed with propylene glycol and mixed until a lotion was obtained.

The compounds considered to be antifungal may be associated to targets as described, but not limited to: [Amaral, A C et al "Therapeutic targets in *Paracoccdioides brasiliensis*: post-transcriptome perspectives" *Gent Mol Res* 4 (2):430-449. 2005]

(i) synthases, such as (a) 1,3-glucan synthase related to virulence of fungi and (b) chitin synthase involved in chitin synthesis of exclusive occurrence in fungi; and (ii) remodeling enzymes, such as (a) mannosyltransferase that is important for cell wall structure, adherence and virulence; (b) transglucosidases involved in the final architecture of the fungus, and (c) hydrolases that have multiple roles in morphogenetic events.

(iii) plasma membrane components, such as: (a) sterol ergosterol that is essential in the cytoplasmic membrane, and the same unique occurrence in fungi; (b) components of the pathway of sphingolipids such as inositol phosphoryl ceramide are distinct fungi, and (c) proton ATPases are essential for the maintenance of cellular homeostasis through regulation of ion exchange of the cell.

(iv) molecular components, such as (a) topoisomerases, which are enzymes that act on replication, transcription, recombination and segregation of chromosomes, and whose differences between human and yeast cells can be exploited by molecular modeling; (b) elongation factors that are required for protein synthesis, as for example, the elongation factor 3 present in fungi and absent in other organisms, including humans; (c) Hsp90 is a protein highly conserved among different organisms and is apparently associated with the pathogenicity of fungi; (d) N-myristoyltransferase responsible for the transfer of myristate to the amino-terminal glycine residue of a number of proteins of eukaryotic cells, is essential for the survival of fungi and whose differences between human and fungal forms are already being revealed; and (e) prenyltransferases responsible for Prenylation of proteins that participate in a variety of cellular functions such as cell growth, differentiation, signal transduction, among others, having poor similarities with human forms.

(v) proteins involved in cell signaling, such as (a) calcineurin, a specific phosphatase for serine-threonine conserved among eukaryotes and plays a crucial role in maintaining cellular homeostasis through control of intracellular calcium under conditions of stress, it is associated with the virulence of the fungus, and (b) TOR, which are proteins related to phosphatidylinositol kinase known for its involvement in cell growth in response to mitogenic signals.

(vi) components of cellular metabolism, such as (a) glyoxylate cycle which is an alternative way in which fungus obtains energy, the enzymes isocitrate lyase and malate synthase participate in the process, (b) urease, which is a metalloenzyme responsible for the hydrolysis of urea in carbamate, increasing the pH. The same is a fungal pathogenic factor, being absent in humans, and (c) urate oxidase, an enzyme of the purine degradation pathway and is involved in the kidnapping of fungal free radicals playing an essential role in their survival, and being that this pathway is absent in humans.

(vii) essential genes, such as (a) Cdc28 and (b) Civ1 that are involved in basic cell cycle of fungi.

The invention claimed is:

1. A benzyl aralkyl ether compound having formula 1-[2-(2,4-dichlorophenyl)-2-{[4-(trifluoromethyl) benzyl] oxy} ethyl]-1H-imidazole or pharmaceutically acceptable salts thereof.

2. A pharmaceutical composition for topical, oral, parenteral or intra-peritoneal administration, comprising as an active ingredient the compound as defined in claim 1, and one or more pharmaceutically acceptable excipients.

3. The pharmaceutical composition according to claim 2, wherein a concentration of the active ingredient is in a range from 0.001 to 1000 mg.

* * * * *

UNITED STATES PATENT AND TRADEMARK OFFICE
CERTIFICATE OF CORRECTION

PATENT NO. : 8,975,289 B2  Page 1 of 1
APPLICATION NO. : 13/389741
DATED : March 10, 2015
INVENTOR(S) : Artur Franz Keppler et al.

It is certified that error appears in the above-identified patent and that said Letters Patent is hereby corrected as shown below:

In the Specification

The drawing of Procedure 2, located in column 12, reads:

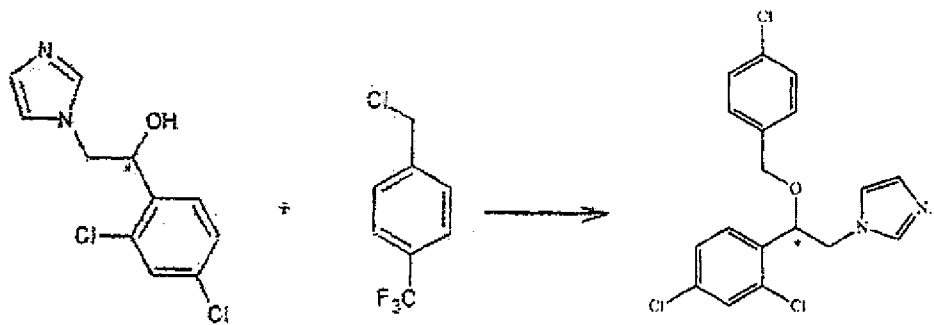

The drawing of Procedure 2, located in column 12, should read:

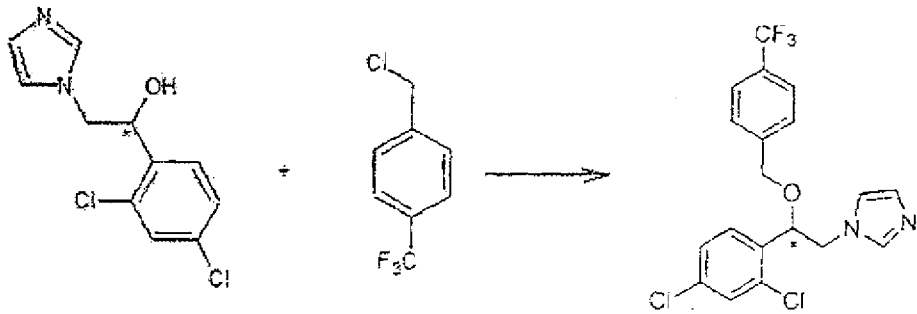

Signed and Sealed this
Twenty-fifth Day of August, 2015

Michelle K. Lee
*Director of the United States Patent and Trademark Office*